US006187564B1

(12) United States Patent
Sytkowski

(10) Patent No.: US 6,187,564 B1
(45) Date of Patent: *Feb. 13, 2001

(54) DNA ENCODING ERYTHROPOIETIN MULTIMERS HAVING MODIFIED 5' AND 3' SEQUENCES AND ITS USE TO PREPARE EPO THERAPEUTICS

(75) Inventor: Arthur J. Sytkowski, Arlington, MA (US)

(73) Assignee: Beth Israel Deaconess Medical Center, Boston, MA (US)

( * ) Notice: Under 35 U.S.C. 154(b), the term of this patent shall be extended for 0 days.

This patent is subject to a terminal disclaimer.

(21) Appl. No.: 09/018,138

(22) Filed: Feb. 3, 1998

Related U.S. Application Data

(63) Continuation-in-part of application No. 08/890,929, filed on Jul. 10, 1997.

(51) Int. Cl.[7] .......................... C12N 15/62; C12N 15/18; C07K 14/505; A61K 38/18

(52) U.S. Cl. ........................ 435/69.7; 536/23.4; 530/350; 514/2; 424/85.1

(58) Field of Search .............................. 530/350; 514/2; 424/85.1; 435/69.7; 536/23.4

(56) References Cited

U.S. PATENT DOCUMENTS

| 4,816,567 | 3/1989 | Cabilly et al. . |
| 4,874,813 | 10/1989 | O'Shannessy . |
| 5,073,627 | 12/1991 | Curtis et al. . |
| 5,091,513 | 2/1992 | Huston et al. . |
| 5,114,711 | 5/1992 | Bell et al. . |
| 5,116,964 | 5/1992 | Capon et al. . |
| 5,225,538 | 7/1993 | Capon et al. . |
| 5,349,053 | 9/1994 | Landolfi . |
| 5,428,130 | 6/1995 | Capon et al. . |
| 5,478,925 * | 12/1995 | Wallach et al. ........................ 530/351 |
| 5,547,852 | 8/1996 | Seiler et al. . |
| 5,580,853 | 12/1996 | Sytkowski . |
| 5,614,184 | 3/1997 | Sytkowski et al. . |
| 5,684,136 | 11/1997 | Godowski . |
| 5,688,679 | 11/1997 | Powell . |
| 5,883,230 | 3/1999 | Schendel . |

FOREIGN PATENT DOCUMENTS

| A-79357 | 1/1992 | (AU) . |
| 0255231B1 | 2/1988 | (EP) . |
| 0 283 244 B1 | 3/1988 | (EP) . |
| 0267678A1 | 5/1988 | (EP) . |
| 0306943A3 | 9/1988 | (EP) . |
| 0 622 459 A1 | 4/1994 | (EP) . |
| 0618227A1 | 5/1994 | (EP) . |
| 0 816 510 A1 | 12/1996 | (EP) . |
| WO 91/19739 | 12/1991 | (WO) . |
| WO 92/04455 | 3/1992 | (WO) . |
| 92/06117 | 4/1992 | (WO) . |
| WO 92/06116 | 4/1992 | (WO) . |
| WO 94/02611 | 3/1994 | (WO) . |
| 94/09817 | 5/1994 | (WO) . |
| 94/13806 | 6/1994 | (WO) . |
| WO 95/25746 | 9/1995 | (WO) . |
| WO 95/33057 | 12/1995 | (WO) . |
| WO 96/19573 * | 6/1996 | (WO) . |
| 97/00319 | 1/1997 | (WO) . |
| WO 97/12985 | 4/1997 | (WO) . |

OTHER PUBLICATIONS

Yamaguchi, K., et al., "Effects of Site–directed Removal of N–Glycosylation Sites in Human Erythropoietin on Its Production and Biological Properties," *J. Biol. Chem.*, 266(30):20434–20439, (Oct. 25, 1991).

Curtis, B., et al., "Enhanced hematopoietic activity of a human granulocyte/macrophage colony–stimulating factor–interleukin 3 fusion protein," *Proc. Natl. Acad. Sci. USA*, 88:5809–5813, (Jul., 1991).

Boissel, J.P., et al., "Erythropoietin Structure–Function Relationships," In *The Biology of Hematopoiesis*, Wiley–Liss, Inc.), pp. 227–232 (1990).

Dubé, S., et al., "Glycosylation at Specific Sites of Erythropoietin Is Essential for Biosynthesis, Secretion, and Biological Function," *J. Biol. Chem.*, 263(33):17516–17521 (Nov. 25, 1988).

Wen, D., et al., "Erythropoietin Structure–Function Relationships: High Degree of Sequence Homology Among Mammals," *Blood*, 82(5): 1507–1516, (Sep. 1, 1993).

Wen, D., et al., "Erythropoietin Structure–Function Relationships: Identification of Functionally Important Domains," *J. Biol. Chem.*, 269(3): 22839–22846, (Sep. 9, 1994).

Boissel, J.P., et al., "Erythropoietin Structure–Function Relationships: Mutant Proteins That Test A Model of Tertiary Structure," *J. Biol. Chem.*, 268(21): 15983–15993, (Jul. 25, 1993).

Chern, Y., et al., "Potention of the Erythropoietin Response by Dimethyl Sulfoxide Priming of Erythroleukemia Cells: Evidence for Interaction of Two Signaling Pathways," *Blood*, 76(11) :2204–2209, (Dec. 1, 1990).

Sytkowski, A., et al., "Immunochemical Studies of Human Erythropoietin Using Site–Specific Anti–peptide Antibodies: Identification of a Functional Domain," *J. Biol. Chem.*, 262(3): 1161–1165, (Jan. 25, 1987).

(List continued on next page.)

*Primary Examiner*—David L. Fitzgerald
(74) *Attorney, Agent, or Firm*—Hamilton, Brook, Smith & Reynolds, P.C.

(57) ABSTRACT

Provided are nucleic acids encoding multimeric erythropoietin (EPO) proteins and having modifications in the 5' and 3' noncoding sequences relative to the corresponding sequences in native EPO DNA. The invention also relates to the use of such nucleic acids to produce multimeric EPO proteins, which may have altered activity as compared to EPO multimers expressed from nucleic acids having native 5' and 3' sequences.

36 Claims, 12 Drawing Sheets

OTHER PUBLICATIONS

Sytkowski, A., et al., "Isolation and Characterization of an Anti–peptide Monoclonal Antibody to Human Erythropoietin," *J. Biol. Chem.*, 260(27): 14727–14731, (Nov. 25, 1985).

Feldman, L., et al., "Four Unique Monoclonal Antibodies to the Putative Receptor Binding Domain of Erythropoietin Inhibit the Biological Function of the Hormone," *Exp. Hematol.*, 20:64–68, (1992).

Fibi, M.R., et al., "N–and O–Glycosylation Muteins of Recombinant Human Erythropoietin Secreted from BHK–21 Cells," *Blood*, 85(5) : 1229–1236, (Mar. 1, 1995).

Takeuchi, M., et al., "Role of Sugar Chains in the in Vitro Biological Activity of Human Erythropoietin Produced in Recombinant Chinese Hamster Ovary Cells," *J. Biol. Chem.*, 265(21): 12127–12130, (Jul. 25, 1990).

Yonekura, S., et al., "Erythropoietin receptors induced by dimethyl sulfoxide exhibit positive cooperativity associated with an amplified biologic response," *Proc. Natl. Acad. Sci. USA*, 88:2535–2539, (Mar. 1991).

Grodberg, J., et al., "Functional and Structural Role of Arginine 103 in Human Erythropoietin," *Arch. Bioch. Bioph.*, 333(2): 427–431, (Sep. 15, 1996).

Chern, Y., et al., "Structural Role of amino acids 99–110 in recombinant human erythropoietin," *Eur. J. Biochem.*, 202: 225–229, (1991).

Grodberg, J., et al., "Alanine scanning mutagenesis of human erythropoietin identifies four amino acids which are critical for biological activity," *Eur. J. Biochem.*, 218: 597–601, (1993)

Jacobs, K., et al., "Isolation and characterization of genomic and cDNA clones of human erythropoietin," *Nature*, 313:806–810, (Feb. 28, 1985).

Hollenbaugh, D., et al., "Cleavable CD40Ig fusion proteins and the binding to sgp39," *J. Immuno. Meth.*, 188: 1–7 (1995).

Sandlie, I., et al., "Engineering the Hinge Region to Optimize Complement–induced Cytolysis," In *Antibody Engineering*, C.A.K. Borrebaeck, eds. (NY: W.H. Freeman and Company) pp. 69–88 (1992).

Hamers–Castermann, C., et al., "Naturally occurring antibodies devoid of light chains," *Nature*, 363: 446–448, (Jun. 2, 1993).

Terskjkh, A.V., et al., "Peptabody: A new type of high avidity binding protein," *Proc. Natl. Acad. Sci. USA*, 94:1663–1668, (Mar. 1997).

McMahon, F.G., et al., "Pharmacokinetics and Effects of Recombinant Human Erythropoietin After Intravenous and Subcutaneous Injections in Healthy Volunteers," *Blood*, 76(9): 1718–1722, (Nov. 1, 1990).

Spivak, J.L., et al., "The In Vivo Metabolism of Recombinant Human Erythropoietin in the Rat," *Blood*, 73(1): 90–99, (Jan. 1989).

Knusli, C., et al., "Polyethylene glycol (PEG) modification of granulocyte–macrophage colony stimulating factor (GM–CSF) enhances neutrophil priming activity but not colony stimulating activity," *British Journal Haematology*, 82: 654–663, (1992).

Satake, R., et al., "Chemical modification of erythropoietin: an increase in in vitro activity by guanidination," *Biochimica et Biophysica Acta*, 1038: 125–129, (1990).

Wrighton, N.C., et al., "Increased potency of an erythropoietin peptide mimetic through covalent dimerzation," *Nature Biotechnology*, 15:1261–1265, (1997).

Welch, N.S., et al., "Interleukin–3/erythropoietin fusion proteins: in vitro effects on hematopoietic cells," *Exp. Hematol.*, 21:647–655 (1993).

Sytkowski, A.J., et al., "An Epo—Epo Fusion Protein with Enhanced Potency and Efficacy in vivo," Thirty–Ninth Annual Meeting of the American Society of Hematology, San Diego, California, USA, Dec. 5–9, 1997. *Blood 90* (10 Suppl. 1 Part 1). 1997. 57A. (Abstract 244).

Lunn, E.D., et al., "Erythropoietin Dimers with Enhanced in vivo Activity in Mice," Thirty–Eighth Annual Meeting of the American Society of Hematology, Orlando, Florida, USA, Dec. 6–10, 1996. *Blood 88* (10 Suppl. 1 Part 1–2). 1996. 543A. (Abstract 2161).

McGary, E.C., et al., "Post–transcriptional Regulation of Erythropoietin mRNA Stability by Erythropoietin mRNA–binding Protein," *The Journal of Biological Chemistry*, 272:8628–8634 (1997).

Batra, J.K., et al., "Insertion of Constant Region Domains of Human $IgG_1$ Into CD4–PE40 Increases its Plasma Half–Life," *Molecular Immunology*, 30:379–386 (1993).*

Jelkmann, W., "Biology of Erythropoietin," *Clin Investig*, 72:S3–S10 (1994).*

Modi, N.B., "Pharmacokinetics and pharmacodynamics of Recombinant Proteins and Peptides," *Journal of Controlled Release*, 29:269–281 (1994).*

* cited by examiner

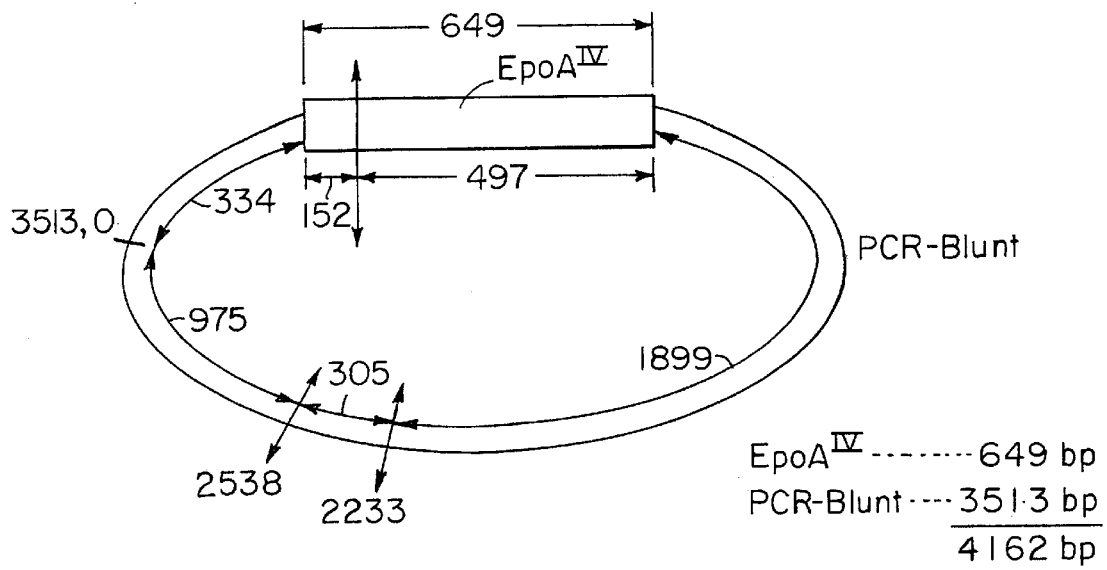
FIG. 6  BglI restriction digests: ① EpoA^IV Forward Direction ⊕
2396bp, 1461bp, 305bp
② EpoA^IV Reverse Direction ⊖
2051bp, 1806bp, 305bp
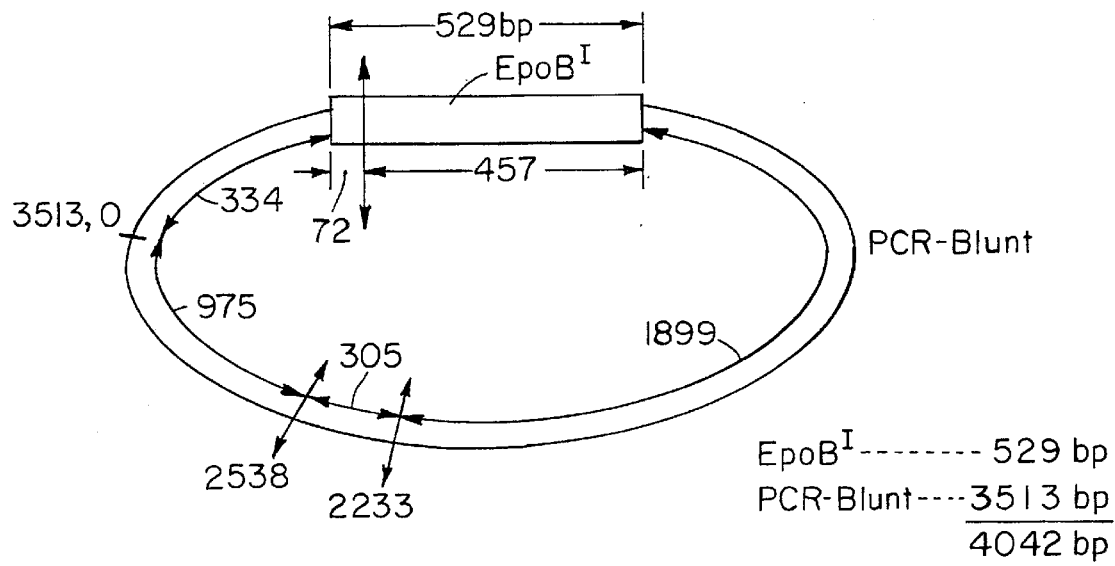
FIG. 7  BglI restriction digests: ① EpoB^I Forward Direction ⊕
2356bp, 1381bp, 305bp
② EpoB^I Reverse Direction ⊖
1971bp, 1766bp, 305bp

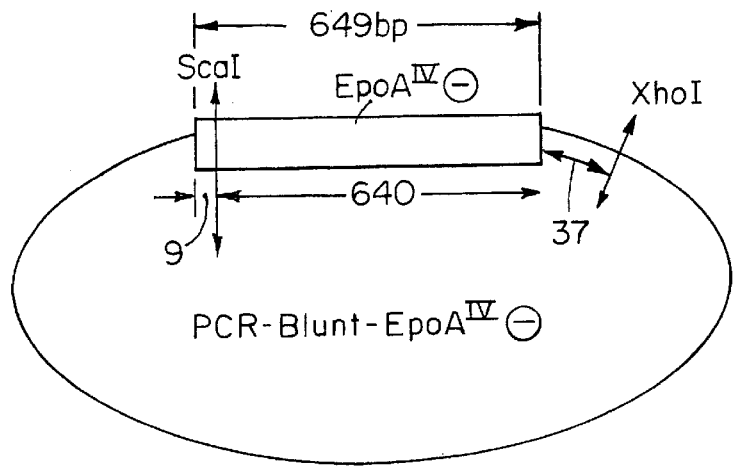
FIG. 8 ScaI and XhoI restriction digests: 3485bp, 6776bp
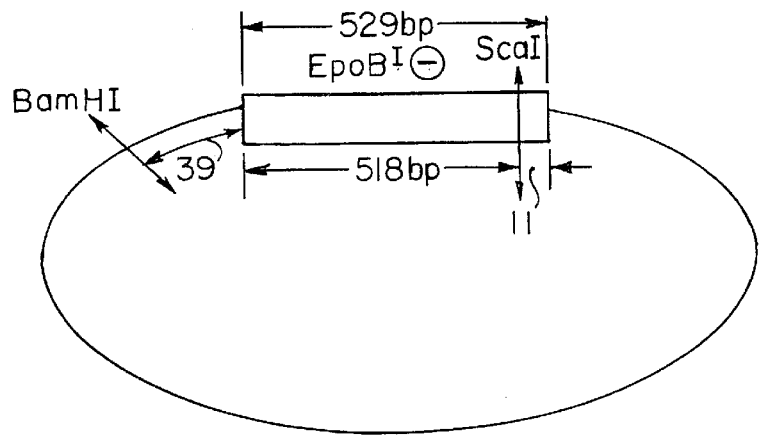
FIG. 9 BamHI and ScaI restriction digests: 3485bp, 5576bp
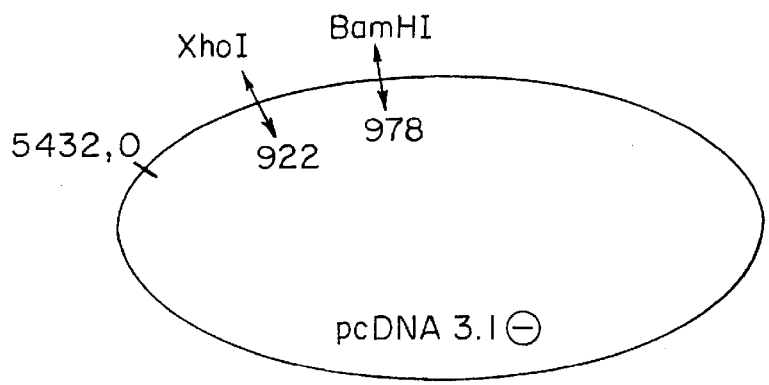
FIG. 10 XhoI and BamHI restriction digest: 5376bp, 56bp NgoMI restriction digest of pcDNA3-1-Epo-Epo: 3931bp, 1342bp, 1054bp, 2836bp

```
              10         20         30         40         50         60
               |          |          |          |          |          |
   1  AAGCTTCTGG GCTTCCAGAC CCAGCTACTT TGCGGAACTC AGCAACCCAG GCATCTCTGA
  61  GTCTCCGCCC AAGACCGGGA TGCCCCCCAG GGGAGGTGTC CGGGAGCCCA GCCTTTCCCA
 121  GATAGCACGC TCCGCCAGTC CCAAGGGTGC GCAACCGGCT GCACTCCCCT CCCGCGACCC
 181  AGGGCCCGGG AGCAGCCCCC ATGACCCACA CGCACGTCTG CAGCAGCCCC GCTCACGCCC
 241  CGGCGAGCCT CAACCCAGGC GTCCTGCCCC TGCTCTGACC CCGGGTGGCC CCTACCCCTG
 301  GCGACCCCTC ACGCACACAG CCTCTCCCCC ACCCCCACCC GCGCACGCAC ACATGCAGAT
 361  AACAGCCCCG ACCCCGGCC AGAGCCGCAG AGTCCCTGGG CCACCCCGGC CGCTCGCTGC
 421  GCTGCGCCGC ACCGCGCTGT CCTCCCGGAG CCGGACCGGG GCCACCGCGC CCGCTCTGCT
 481  CCGACACCGC GCCCCCTGGA CAGCCGCCCT CTCCTCTAGG CCCGTGGGGC TGGCCCTGCA
 541  CCGCCGAGCT TCCCGGGATG AGGGCCCCCG GTGTGGTCAC CCGGCGCGCC CCAGGTCGCT
 601  GAGGGACCCC GGCCAGGCGC GGAGATGGGG GTGCACGGTG AGTACTCGCG GGCTGGGCGC
 661  TCCCGCCGCC CGGGTCCCTG TTTGAGCGGG GATTTAGCGC CCCGGCTATT GGCCAGGAGG
 721  TGGCTGGGTT CAAGGACCGG CGACTTGTCA AGGACCCCGG AAGGGGGAGG GGGGTGGGGC
 781  AGCCTCCACG TGCCAGCGGG GACTTGGGGG AGTCCTTGGG GATGGCAAAA ACCTGACCTG
 841  TGAAGGGGAC ACAGTTTGGG GGTTGAGGGG AAGAAGGTTT GGGGGTTCTG CTGTGCCAGT
 901  GGAGAGGAAG CTGATAAGCT GATAACCTGG GCGCTGGAGC CACCACTTAT CTGCCAGAGG
 961  GGAAGCCTCT GTCACACCAG GATTGAAGTT TGGCCGGAGA AGTGGATGCT GGTAGCTGGG
1021  GGTGGGGTGT GCACACGGCA GCAGGATTGA ATGAAGGCCA GGGAGGCAGC ACCTGAGTGC
1081  TTGCATGGTT GGGGACAGGA AGGACGAGCT GGGGCAGAGA CGTGGGGATG AAGGAAGCTG
1141  TCCTTCCACA GCCACCCTTC TCCCTCCCCG CCTGACTCTC AGCCTGGCTA TCTGTTCTAG
1201  AATGTCCTGC CTGGCTGTGG CTTCTCCTGT CCCTGCTGTC GCTCCCTCTG GGCCTCCCAG
1261  TCCTGGGCGC CCCACCACGC CTCATCTGTG ACAGCCGAGT CCTGGAGAGG TACCTCTTGG
1321  AGGCCAAGGA GGCCGAGAAT ATCACGGTGA GACCCCTTCC CCAGCACATT CCACAGAACT
```

Figure 13A

```
1381  CACGCTCAGG GCTTCAGGGA ACTCCTCCCA GATCCAGGAA CCTGGCACTT GGTTTGGGGT
1441  GGAGTTGGGA AGCTAGACAC TGCCCCCCTA CATAAGAATA AGTCTGGTGG CCCCAAACCA
1501  TACCTGGAAA CTAGGCAAGG AGCAAAGCCA GCAGATCCTA CGGCCTGTGG GCCAGGGCCA
1561  GAGCCTTCAG GGACCCTTGA CTCCCCGGGC TGTGTGCATT TCAGACGGGC TGTGCTGAAC
1621  ACTGCAGCTT GAATGAGAAT ATCACTGTCC CAGACACCAA AGTTAATTTC TATGCCTGGA
1681  AGAGGATGGA GGTGAGTTCC TTTTTTTTTT TTTTTCCTTT CTTTTGGAGA ATCTCATTTG
1741  CGAGCCTGAT TTTGGATGAA AGGGAGAATG ATCGGGGGAA AGGTAAAATG GAGCAGCAGA
1801  GATGAGGCTG CCTGGGCGCA GAGGCTCACG TCTATAATCC CAGGCTGAGA TGGCCGAGAT
1861  GGGAGAATTG CTTGAGCCCT GGAGTTTCAG ACCAACCTAG GCAGCATAGT GAGATCCCCC
1921  ATCTCTACAA ACATTTAAAA AAATTAGTCA GGTGAAGTGG TGCATGGTGG TAGTCCCAGA
1981  TATTTGGAAG GCTGAGGCGG GAGGATCGCT TGAGCCCAGG AATTTGAGGC TGCAGTGAGC
2041  TGTGATCACA CCACTGCACT CCAGCCTCAG TGACAGAGTG AGGCCCTGTC TCAAAAAGA
2101  AAAGAAAAAA GAAAAATAAT GAGGGCTGTA TGGAATACAT TCATTATTCA TTCACTCACT
2161  CACTCACTCA TTCATTCATT CATTCATTCA ACAAGTCTTA TTGCATACCT TCTGTTTGCT
2221  CAGCTTGGTG CTTGGGGCTG CTGAGGGGCA GGAGGGAGAG GGTGACATGG GTCAGCTGAC
2281  TCCCAGAGTC CACTCCCTGT AGGTCGGGCA GCAGGCCGTA GAAGTCTGGC AGGGCCTGGC
2341  CCTGCTGTCG GAAGCTGTCC TGCGGGCCA GGCCCTGTTG GTCAACTCTT CCCAGCCGTG
2401  GGAGCCCCTG CAGCTGCATG TGGATAAAGC CGTCAGTGGC CTTCGCAGCC TCACCACTCT
2461  GCTTCGGGCT CTGGGAGCCC AGGTGAGTAG GAGCGGACAC TTCTGCTTGC CCTTTCTGTA
2521  AGAAGGGGAG AAGGGTCTTG CTAAGGAGTA CAGGAACTGT CCGTATTCCT TCCCTTTCTG
2581  TGGCACTGCA GCGACCTCCT GTTTTCTCCT TGGCAGAAGG AAGCCATCTC CCCTCCAGAT
2641  GCGGCCTCAG CTGCTCCACT CCGAACAATC ACTGCTGACA CTTTCCGCAA ACTCTTCCGA
2701  GTCTACTCCA ATTTCCTCCG GGGAAAGCTG AAGCTGTACA CAGGGGAGGC CTGCAGGACA
2761  GGGGACAGAT GACCAGGTGT GTCCACCTGG GCATATCCAC CACCTCCCTC ACCAACATTG
2821  CTTGTGCCAC ACCCTCCCCC GCCACTCCTG AACCCCGTCG AGGGGCTCTC AGCTCAGCGC
2881  CAGCCTGTCC CATGGACACT CCAGTGCCAG CAATGACATC TCAGGGGCCA GAGGAACTGT
2941  CCAGAGAGCA ACTCTGAGAT CTAAGGATGT CACAGGGCCA ACTTGAGGGC CCAGAGCAGG
```

Figure 13B

```
3001  AAGCATTCAG AGAGCAGCTT TAAACTCAGG GACAGAGCCA TGCTGGGAAG ACGCCTGAGC
3061  TCACTCGGCA CCCTGCAAAA TTTGATGCCA GGACACGCTT TGGAGGCGAT TTACCTGTTT
3121  TCGCACCTAC CATCAGGGAC AGGATGACCT GGAGAACTTA GGTGGCAAGC TGTGACTTCT
3181  CCAGGTCTCA CGGGCATGGG CACTCCCTTG GTGGCAAGAG CCCCCTTGAC ACCGGGGTGG
3241  TGGGAACCAT GAAGACAGGA TGGGGGCTGG CCTCTGGCTC TCATGGGGTC CAAGTTTTGT
3301  GTATTCTTCA ACCTCATTGA CAAGAACTGA AACCACCAAT ATGACTCTTG GCTTTTCTGT
3361  TTTCTGGGAA CCTCCAAATC CCCTGGCTCT GTCCCACTCC TGGCAGCAGT GCAGCAGGTC
3421  CAGGTCCGGG AAATGAGGGG TGGAGGGGGC TGGGCCCTAC GTGCTGTCTC ACACAGCCTG
3481  TCTGACCTCT CGACCTACCG GCCTAGGCCA CAAGCTCTGC CTACGCTGGT CAATAAGGTG
3541  TCTCCATTCA AGGCCTCACC GCAGTAAGGC AGCTGCCAAC CCTGCCCAGG GCAAGGCTGC
3601  AG
```

Figure 13C

```
             10         20         30         40         50         60
              |          |          |          |          |          |
  1   CCACCCCGGC CGCTCGCTGC GCTGCGCCGC ACCGCGCTGT CCTCCCGGAG CCGGACCGGG
 61   GCCACCGCGC CCGCTCTGCT CCGACACCGC GCCCCCTGGA CAGCCGCCCT CTCCTCTAGG
121   CCCGTGGGGC TGGCCCTGCA CCGCCGAGCT TCCCGGGATG AGGGCCCCCG GTGTGGTCAC
181   CCGGCGCGCC CCAGGTCGCT GAGGGACCCC GGCCAGGCGC GGAG
```
                                                             Figure 14A Total number of bases is: 224.

```
             10         20         30         40         50         60
              |          |          |          |          |          |
  1   CCACCCCGGC CGCTCGCTGC GCTGCGCCGC ACCGCGCTGT CCTCCCGGAG CCGGACCGGG
 61   GCCACCGCGC CCGCTCTGCT CCGACACCGC GCCCCCTGGA TCCCGGGATG AGGGCCCCCG
121   GTGTGGTCAC CCGGCGCGCC CCAGGTCGCT GAGGGACCCC GGCCAGGCGC GGAG
```
                                                             Figure 14B Total number of bases is: 174.

```
             10         20         30         40         50         60
              |          |          |          |          |          |
  1   CCACCCCGGC CGCTCGCTGC GCTGCGCCGC ACCGCGCTGT CCTCCCGGAG CCGGACCGGG
 61   GCCACCGCGC CCGCTCTGCT CCGACACCGC GCCCCCTGGA CAGCCGCCCT CTCCTCTAGG
121   CCCGTGGGGC TGGCCCTGCA CCGCCGAGCT GAGGGACCCC GGCCAGGCGC GGAG
```
                                                             Figure 14C Total number of bases is: 174.

```
             10         20         30         40         50         60
              |          |          |          |          |          |
  1   CAGCCGCCCT CTCCTCTAGG CCCGTGGGGC TGGCCCTGCA CCGCCGAGCT TCCCGGGATG
 61   AGGGCCCCCG GTGTGGTCAC CCGGCGCGCC CCAGGTCGCT GAGGGACCCC GGCCAGGCGC
121   GGAG
```
                                                             Figure 14D Total number of bases is: 124.

```
             10         20         30         40         50         60
              |          |          |          |          |          |
  1   TCCCGGGATG AGGGCCCCCG GTGTGGTCAC CCGGCGCGCC CCAGGTCGCT GAGGGACCCC
 61   GGCCAGGCGC GGAG
```
                                                             Figure 14E Total number of bases is: 74.

```
             10         20         30         40         50         60
              |          |          |          |          |          |
  1   CCAGGTCGCT GAGGGACCCC GGCCAGGCGC GGAG
```
                                                             Figure 14F Total number of bases is: 34.

```
              10         20         30         40         50         60
               |          |          |          |          |          |
   1   CCAGGTGTGT CCACCTGGGC ATATCCACCA CCTCCCTCAC CAACATTGCT GTGCCACAC
  61   CCTCCCCCGC CACTCCTGAA CCCCGTCGAG GGGCTCTCAG CTCAGCGCCA CCTGTCCCA
 121   TGGACACTCC AGTGCCAGCA ATGACATCTC AGGGGCCAGA GGAACTGTCC GAGAGCAAC
 181   TCTGAGATCT AAGGATGTCA
                                                          Figure 15A
Total number of bases is: 200.

10         20         30         40         50         60
               |          |          |          |          |          |
   1   CCAGGTGTGT CCACCTGGGC ATATCCACCA CCTCCCTCAC CAACATTGCT GTGCCACAC
  61   CCTCCCCCGC CACTCCTGAA CCCCGTCGAG GGGCTCTCAG CTCAGCGCCA CCTGTCCCA
 121   TGGACACTCC AGTGCCAGCA ATGACATCTC
                                                          Figure 15B
Total number of bases is: 150.

10         20         30         40         50         60
               |          |          |          |          |          |
   1   CCAGGTGTGT CCACCTGGGC ATATCCACCA CCTCCCTCAC CAACATTGCT GTGCCACAC
  61   CCTCCCCCGC CACTCCTGAA CCCCGTCGAG GGGCTCTCAG
                                                          Figure 15C
Total number of bases is: 100.

10         20         30         40         50         60
               |          |          |          |          |          |
   1   CCAGGTGTGT CCACCTGGGC ATATCCACCA CCTCCCTCAC CAACATTGCT
                                                          Figure 15D
Total number of bases is: 50.

10         20         30         40         50         60
               |          |          |          |          |          |
   1   CCAGGTGTGT CCACCTGGGC ATATCCACCC AGTGCCAGCA ATGACATCTC GGGGCCAGA
  61   GGAACTGTCC AGAGAGCAAC TCTGAGATCT AAGGATGTCA
                                                          Figure 15E
Total number of bases is: 100.
```

DNA ENCODING ERYTHROPOIETIN MULTIMERS HAVING MODIFIED 5' AND 3' SEQUENCES AND ITS USE TO PREPARE EPO THERAPEUTICS

RELATED APPLICATION(S)

This application is a continuation-in-part application of U.S. Ser. No. 08/890,929, filed Jul. 10, 1997, the teachings of which are incorporated herein by reference, in their entirety.

GOVERNMENT SUPPORT

This invention was made, in whole or in part, with Government support under Contract No. N000014-93-1-0776 awarded by the U.S. Navy and National Institutes of Health Grant No. R01 DK38841. The Government has certain rights in the invention.

BACKGROUND OF THE INVENTION

A problem encountered in the practice of medicine when using proteins as injectable pharmaceuticals is the frequency at which those injections must be made in order to maintain a therapeutic level of the protein in the circulation. For example, erythropoietin has a relatively short plasma half-life (Spivak, J. L., and Hogans, B. B., *Blood*, 73:90, 1989; McMahon, F. G., et al., *Blood*, 76:1718, 1990). Therefore, therapeutic plasma levels are rapidly decreased, and repeated intravenous administrations must be made. An alternative route of administration is subcutaneous injection. This route offers slower absorption from the site of administration, thus causing a sustained release effect. However, significantly lower plasma levels are achieved and, thus, a similar frequency of injection, as is required with intravenous administration, must be used to produce a comparable therapeutic effect.

Modification of naturally occurring proteins which have therapeutic value is often attempted in an effort to increase the protein's biological activity. Several methods have been employed to increase the biological activity of therapeutic proteins. These methods often focus on increasing the size of the therapeutic agents. For example, the size of a protein can be increased through chemical conjugation with a reagent such as polyethylene glycol (PEG) (Knusli, C., et al., *Brit. J. Haematol.* 82:654–663, 1992). This procedure, also known as "PEGylation", has been reported with several protein agents, first as a means to reduce antigenicity, but also as a way to increase biological activity.

Another method of increasing a protein's size is through chemical cross-linking with another protein. For example, to increase the antigenicity of a protein, chemical cross-linking agents are used to conjugate the immunogenic protein to a carrier molecule such as immunoglobulin or serum albumin.

However, the conjugation of chemical compounds or inert molecules to a protein often results in a significant decrease of the overall biological activity, and of selected biological activity of the protein. (Knusli, C., et al., *Brit. J. Haematol.*, 82:654–663, 1992). These conjugations must be designed such that the resulting modified protein remains therapeutically efficacious and retains the desired biological properties of the unmodified, wild type (i.e., naturally-occurring) protein (Satake, R., et al., *Biochem. Biophys. Acta.* 1038:125–129, 1990). Thus, it would be advantageous to be able to modify therapeutically active proteins to increase their biological activity which would result in less frequent injections or smaller doses of protein.

SUMMARY OF THE INVENTION

The present invention relates to modified proteins or polypeptides with increased biological activity, and methods of producing and using these modified proteins and polypeptides.

Increased biological activity results from the production of fusion proteins that result in protein multimers, e.g., dimers and trimers. Protein multimers are produced by expressing tandemly linked nucleic acids encoding the proteins of the present invention, or biologically active fragments, analogs, variants, mutants or derivatives of the proteins. The nucleic acids that encode the proteins are fused, as described herein. The proteins of the present invention can be fused directly to another protein, or can be fused via a linker, e.g., a peptide linker. The tandemly fused nucleic acid sequence is then inserted into an expression vector and introduced into a competent cell, either prokaryotic or eukaryotic, resulting in the production of a fusion protein multimer with increased biological activity.

Increased biological activity is defined herein as a prolonged plasma half-life (that is, a longer circulating half-life relative to the naturally occurring protein), and/or higher potency (i.e., requiring a smaller quantity relative to the naturally occurring protein to achieve a specified level of biological activity). Increased biological activity can also encompass a combination of the above-described activities, for example, a modified protein with higher potency that also exhibits a prolonged circulating half-life. Because the proteins of the present invention have increased biological activity, the frequency with which they must be administered is reduced, or the amount administered to achieve an effective dose is reduced. Additional advantages can also result from the modifications described herein. For example, new unpredictable activities can result, such as increased affinity for receptors or binding ligands, which can result in increased stimulation of signal generated by such binding. A reduced quantity of modified protein would then be necessary over the course of treatment as compared to the quantity necessary if unmodified protein were used.

Proteins encompassed by the present invention include any protein with therapeutic activity. Specifically encompassed by the present invention are cytokines, growth factors, and hormones which include, for example, the following: Interferon-α, Interferon-β, Interferon-γ, Interleukin-1, Interleukin-2, Interleukin-3, Interleukin-4, Interleukin-5, Interleukin-6, Interleukin-7, Interleukin-8, Interleukin-9, Interleukin-10, Interleukin-11, Interleukin-12, Interleukin-13, Interleukin-14, Interleukin-15, Interleukin-16, Erythropoietin, Colony-Stimulating Factor-1, Granulocyte Colony-Stimulating Factor, Granulocyte-Macrophage Colony-Stimulating Factor, Leukemia Inhibitory Factor, Tumor Necrosis Factor, Lymphotoxin, Platelet-Derived Growth Factor, Fibroblast Growth Factors, Vascular Endothelial Cell Growth Factor, Epidermal Growth Factor, Transforming Growth Factor-β, Transforming Growth Factor-α, Thrombopoietin, Stem Cell Factor, Oncostatin M, Amphiregulin, Mullerian-Inhibiting Substance, B-Cell Growth Factor, Macrophage Migration Inhibiting Factor, Endostatin, and Angiostatin. Descriptions of these proteins can be found in "Human Cytokines: *Handbook for Basic and Clinical Research*", Aggarwal, B. B., and Gutterman, J. U., Eds., Blackwell Scientific Publications, Boston, Mass., (1992), which is herein incorporated by reference in its entirety.

More specifically, the present invention relates to modified erythropoietin with increased biological activity, as defined herein. The modified erythropoietin with increased biological activity of the present invention is a fusion protein comprising two or more erythropoietin molecules covalently fused, resulting in an erythropoietin multimer.

Also encompassed by the present invention are methods of making and using the fusion protein multimers described herein and methods of using them.

BRIEF DESCRIPTION OF THE DRAWINGS

FIG. 6 is a diagram showing the restriction digest of pCRBlunt-EPO $A^{IV}$ with Bgl I.

FIG. 7 is a diagram showing the restriction digest of pCRBlunt-EPO $B^I$ with Bgl I.

FIG. 8 is a diagram showing the restriction digest of pCR2lunt-EPO $A^{IV}(-)$.

FIG. 9 is a diagram showing the restriction digest of pCRBlunt-EPO $B^I(-)$.

FIG. 10 is a diagram showing the Xho I and BamH I restriction digest of pcDNA3.1(-).

FIGS. 13A–C depict the nucleotide sequence of the human EPO gene (SEQ ID NO:1).

FIGS. 14A–F depict the nucleic acid sequence of nucleotides 401–624 in the 5' untranslated region of the EPO gene (SEQ ID NO:2) (FIG. 14A) and five variant sequences (SEQ ID NOS: 3–7) (FIGS. 14B–F).

FIGS. 15A–E depicts the nucleic acid sequence of nucleotides 2773–2972 in the 3' untranslated region of the EPO gene (SEQ ID NO:8) (FIG. 15A) and four variant sequences (SEQ ID NOS: 9–12) (FIGS. 15B–E).

DETAILED DESCRIPTION OF THE INVENTION

Figure 1:
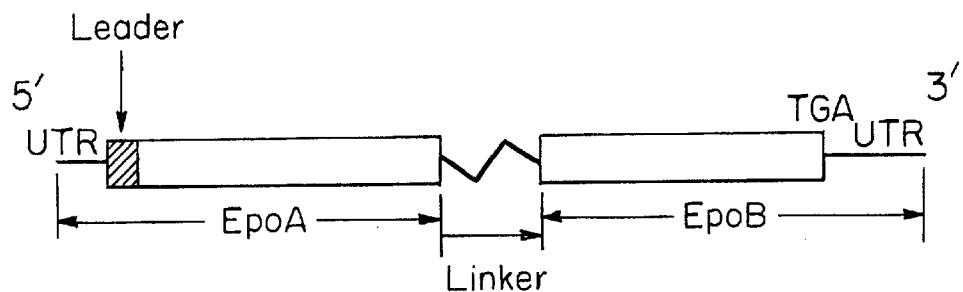
FIG. 1 is a diagram showing an EPO—EPO dimer DNA construct comprising an EPO A cDNA linked to an EPO B cDNA via a linker sequence.

As used herein, the term fusion protein refers to a C-terminal to N-terminal fusion of one protein molecule to another protein molecule. The fusion proteins of the present invention typically include constructs in which a linker peptide sequence is utilized. The fusion proteins of the present invention have a formula of $R_1$–$R_2$ or $R_1$-L-$R_2$, where $R_1$ and $R_2$ are substantially similar or identical protein molecules and L is a linker, typically a peptide. In another embodiment of the present invention, $R_1$ and $R_2$ can be different proteins. The protein molecules are fused to one another in such a manner as to produce a single fusion protein comprised of two or more protein molecules. The fusion protein produced has increased biological activity. In one embodiment of the present invention the protein molecules are EPO.

Fusion protein constructs are named by listing the respective molecules. For example, EPO-L-EPO refers to a fusion protein comprised of two EPO molecules joined by a peptide linker, and EPO-L-EPO-L-EPO refers to a fusion protein comprised of three EPO molecules joined by two peptide linkers.

The term "recombinant", as used herein, means that a host protein is derived from recombinant (e.g., eukaryotic or prokaryotic host cell) expression systems which include, for example, yeast (e.g., Saccharomyces), bacteria (such as, Escherichia or Bacillus), and animal cells including insect or mammalian expression systems. Proteins expressed in most bacterial cultures will be free of glycan. Protein expressed in yeast may have a glycosylation pattern different from protein expressed in mammalian cells.

As used herein, the term nucleotide sequence or nucleic acid sequence refers to a heteropolymer of deoxyribonucleotides (DNA) or ribonucleotides (RNA). Nucleic acid sequences encoding the proteins provided in this invention can be assembled from DNA, either cDNA or genomic DNA, or RNA, and short oligonucleotide linkers to provide a synthetic nucleic acid sequence which is capable of being expressed in a recombinant transcriptional unit.

Homologous nucleic acids, including DNA or RNA, can be detected and/or isolated by hybridization (e.g., under high stringency conditions or moderate stringency conditions). "Stringency conditions" for hybridization is a term of art which refers to the conditions of temperature and buffer concentration which permit hybridization of a particular nucleic acid to a second nucleic acid in which the first nucleic acid may be perfectly complementary to the second, or the first and second may share some degree of complementarity which is less than perfect. For example, certain high stringency conditions can be used which distinguish perfectly complementary nucleic acids from those of less complementarity. "High stringency conditions" and "moderate stringency conditions" for nucleic acid hybridizations are explained in several technical protocol reference texts, for example, Ausubel, F. M., et al., "*Current Protocols in Molecular Biology*" (1995), the teachings of which are hereby incorporated by reference. The exact conditions which determine the stringency of hybridization depend not only on ionic strength, temperature and the concentration of destabilizing agents such as formamide, but also on factors such as the length of the nucleic acid sequence, base composition, percent mismatch between hybridizing sequences and the frequency of occurrence of subsets of that sequence within other non-identical sequences. Thus, high or moderate stringency conditions could be determined for detecting the various forms of recombinant polypeptides.

By varying hybridization conditions from a level of stringency at which no hybridization occurs to a level at which hybridization is first observed, conditions which will allow a given sequence to hybridize (e.g., selectively) with the sequences, with substantially similar identity in the sample can be determined.

Exemplary conditions are described in Krause, M. H. and Aaronson, S. A., *Methods in Enzymology*, 200:546–556, 1991. Also, "*Current Protocols in Molecular Biology*" (supra), which describes how to determine washing conditions for moderate or low stringency conditions. Washing is the step in which conditions are usually set so as to determine a minimum level of complementarity of the hybrids. Generally, starting from the lowest temperature at which only homologous hybridization occurs, each ° C. by which the final wash temperature is reduced (holding SSC concentration constant) allows an increase by 1% in the maximum extent of mismatching among the sequences that hybridize. Generally, doubling the concentration of SSC results in an increase in $T_m$ of −17° C. Using these guidelines, the washing temperature can be determined for high, moderate or low stringency, depending on the level of mismatch sought. For example, in this invention alterations in the noncoding (5' and 3' untranslated) regions of the gene may necessitate changes in stringency conditions from low to medium to high depending upon the number of nucleotides that are modified that differ from the condition used to detect wild type versions of the gene. Where appropriate the salt concentrations and temperatures will be adjusted accordingly.

The term recombinant expression vector, as used herein, refers to a replicable DNA construct used either to amplify or to express DNA which encodes the fusion proteins of the present invention. The recombinant expression vector includes a transcriptional unit comprising an assembly of (1) a genetic element or elements having a regulatory role in gene expression, for example, promoters or enhancers; (2) a structural or coding sequence which is transcribed into mRNA and translated into protein; and (3) appropriate transcription and translation initiation and termination sequences. Structural elements intended for use in yeast expression systems preferably include a leader sequence enabling extracellular secretion of translated protein by a host cell. Alternatively, where recombinant protein is expressed without a leader sequence or transport sequence, it may include an N-terminal methionine residue. This residue may optionally be subsequently cleaved from the expressed recombinant protein to provide a final product.

A DNA sequence encoding a fusion protein is constructed using recombinant DNA techniques to assemble separate DNA fragments encoding proteins into an appropriate expression vector. For example, the 3' end of a DNA molecule encoding a protein is ligated to the 5' end of a second DNA molecule encoding the same or a substantially similar protein, with the reading frames of the sequences in phase to permit mRNA translation of the sequences into a single biologically active fusion protein. The DNA molecules are joined in tandem, meaning that the DNA molecules are joined in succession, one after the other. The regulatory elements responsible for transcription of DNA into mRNA are retained on the first of the two DNA sequences while binding signals or stop codons, which would prevent read-through to the second DNA sequence, are eliminated. Conversely, regulatory elements are removed from the second DNA sequence while stop codons required to end translation are retained.

As described herein, means are provided for linking protein molecules, preferably via a linker sequence(s). The linker sequence(s) separates the protein molecules by a distance sufficient to ensure that each protein molecule properly folds into its secondary and tertiary structures. Suitable linker sequences (1) adopt a conformation suitable to result in a fusion protein with increased biological activity, (2) do not exhibit a propensity for developing an ordered secondary structure which could impair the biological functions of the protein molecules, and (3) have minimal hydrophobic or charged character which could impair the biological functions of the EPO molecules. For example, a suitable linker will produce a fusion protein where interaction of the protein components results in increased biological activity. The linker conformation can be flexible or rigid, depending on the final conformation of the fusion required to result in increased biological activity. An example of a more rigid linker would be a linker with an α-helix that would not allow free rotation of the linked protein components. Typical surface amino acids in flexible protein regions include Glycine (Gly), Asparagine (Asn) and Serine (Ser). Virtually any permutation of amino acid sequences containing Glycine (Gly), Asparagine (Asn) and Serine (Ser) would be expected to satisfy the above criteria for linker sequence. Other near neutral amino acids, such as Threonine (Thr) and Alanine (Ala), may also be used in the linker sequence.

The length of the linker sequence may vary without significantly affecting the biological activity of the fusion protein. Generally, the protein, e.g., EPO, molecules will be separated by a linker sequence having a length of about 10 amino acids to about 20 amino acids, although longer linker sequences may be used, for example, a full-length polypeptide can comprise the linker. In the most preferred aspects of the present invention, the linker sequence is about 15 amino acids in length. The linker sequence is incorporated into the fusion protein by well-known methods and as described in Example 1.

In one embodiment, the fusion proteins described herein comprise wild type (e.g., naturally-occurring) proteins with therapeutic activity. As defined herein, therapeutic activity means the ability of a fusion protein, upon administration to a mammal, to alleviate, to any degree, or eliminate the deficiency or condition for which the mammal is being treated. Specifically encompassed by the present invention are cytokines, growth factors, and hormones which include, for example, the particular proteins listed in the following paragraphs followed by the appropriate reference(s). Each of the references in the following paragraphs is incorporated by reference in its entirety.

INTERFERON-α: Henco, K., et al., *J. Mol. Biol.*, 185: 227–260 (1985). Pestka, S., et al., *Ann. Rev. Biochem.*, 56: 727–777 (1987). *Methods in Enzymology*, Pestka, S., (Ed.), Academic Press, New York, N.Y., 119:3–14 (1986).

INTERFERON-β: "*Human Cytokines: Handbook for Basic and Clinical Research*", Aggarwal, B. B., and Gutterman, J. U. (Eds.), Blackwell Scientific Publications, Boston, Mass. (1992).

INTERFERON-γ: Gray, P. W., et al., *Nature*, 298:859–863 (1982). Rinderknecht, E., et al., *J. Biol. Chem.*, 259:6790–6797 (1984).

INTERLEUKIN-1: IL-1α: Furutani, Y., et al., *Nucleic Acids Res.*, 143:167–3179 (1986). IL-1β: Clark, B. D., et al., *Nucleic Acids Res.* 14:7897–7914 (1986).

INTERLEUKIN-2: Fujita et al., 1983. Durand, D. B., et al., *Mol. Cell Biol.*, 8:1715–1724 (1988).

INTERLEUKIN-3: Yang, Y. C., et al., *Cell*, 47:3–10 (1986).

INTERLEUKIN-4: Arai, N., et al., *J. Immunol.*, 142:274–282 (1989).

INTERLEUKIN-5: Azuma, C., et al., *Nucleic Acids Res.*, 14:9149–9158 (1986). Yokota, T., et al., *Proc. Natl. Acad. Sci. USA*, 84:7388–7392 (1987).

INTERLEUKIN-6: Hirano, T., et al., *Nature*, 324:73–76 (1986). Van Snick, J., et al., *Eur. J. Immunol.*, 18:193–197 (1988).

INTERLEUKIN-7: Goodwin, R. G., et al., *Proc. Natl. Acad. Sci. USA*, 86:302–306 (1989).

INTERLEUKIN-8: Kusner, D. J., et al., *Kidney International* 39:1240–1248 (1991).

INTERLEUKIN-9: Renauld, J-C., et al., *J. Immunol.*, 144:4235–4241 (1990). Moeller, J., et al., *J. Immunol.* 144:4231–4234 (1990). Yang, Y. C., et al., *Blood*, 74:1880–1884 (1989).

INTERLEUKIN-10: Moore, K. W., et al., *Science*, 248:1230–1234 (1990). Fiorentino, D. F., et al., *J. Exp. Med.*, 170:2081–2095 (1989).

INTERLEUKIN-11: Paul, S. R., et al., *Proc. Natl. Acad. Sci. USA*, 87:7512–7516 (1990).

INTERLEUKIN-12: Wolf, S. F., et al., *J. Immunol.*, 146:3074–3081 (1991); BLAST Database (www.ncib.nlm.nih.gov), accession number M65290.

INTERLEUKIN-13: Dolganov, G., *Blood*, 87:3316–3326 (1996).

INTERLEUKIN-14: Ambrus, J. L., et al., *Proc. Natl. Acad. Sci. USA*, 90:6330–6334 (1993).

INTERLEUKIN-15: Meazza, R., et al., *Oncogene*, 12:2187–2192 (1996).

INTERLEUKIN-16: Cruikshank, W. W., et al., *Proc. Natl. Acad. Sci. USA*, 91:5109–5113 (1994).

ERYTHROPOIETIN: Jacobs, K., et al., *Nature*, 313:806–810 (1985).

COLONY-STIMULATING FACTOR-1: Kawasaki, E. S., et al., *Science*, 230:291–296 (1985). Wong, G. G., et al., *Science*, 235:1504–1508 (1987). Ladner, M. B., et al., *EMBO. J.*, 6:2693–2698 (1987). Cerretti, D. P., et al., *Mol. Immunol.*, 25:761–770 (1988). "Colony Stimulating Factors", Dexter, T. M., et al. (Eds.), Marcel Dekker Publishers, New York, N.Y. pp. 155–176 (1990).

GRANULOCYTE-COLONY-STIMULATING FACTOR: Nagata, S., et al., *Nature*, 319:415–418 (1986). Souza, L. M., et al., *Science*, 232:61–65 (1986).

GRANULOCYTE-MACROPHAGE COLONY-STIMULATING FACTOR: Miyataka, S., et al., *EMBO J.*, 4:2561–2568 (1985).

LEUKEMIA INHIBITORY FACTOR: Moureau, J-F., et al., *Nature*, 336:690–692 (1988).

TUMOR NECROSIS FACTOR: Nedwin, G. E., et al., *Nucleic Acids Res.*, 13:6361–6373 (1985).

LYMPHOTOXIN: Nedwin, G. E., et al., *J. Cell Biochem.*, 29:171–182 (1985).

PLATELET-DERIVED GROWTH FACTOR: Deuel, T. F., et al., *J. Biol. Chem.*, 256:8896–8899 (1981). "Human Cytokines: Handbook for Basic and Clinical Research", Aggarwal, B. B., and Gutterman, J. U. (Eds.), Blackwell Scientific Publications, Boston, Mass. (1992).

FIBROBLAST GROWTH FACTORS: Abraham, J. A., et al., *Science*, 233:545–547 (1986a).

VASCULAR ENDOTHELIAL CELL GROWTH FACTOR: Keck, P. J., et al., *Science*, 246:1309–1312 (1989).

EPIDERMAL GROWTH FACTOR: Scott, J., et al., *Science*, 221:236–240 (1983). Gray, A., et al., *Nature*, 303:722–725 (1983).

TRANSFORMING GROWTH FACTOR-β: Derynck, R., et al., *Nature*, 316:701–705 (1985). Scotto, L., et al., *J. Biol. Chem.*, 265:2203–2208 (1990).

TRANSFORMING GROWTH FACTOR-α: Derynck, R., *Cell*, 54:593–595 (1988).

THROMBOPOIETIN: Sohma, Y., et al., *FEBS Lett.*, 353: 57–61 (1994); BLAST Database (www.ncib.nlm.nih.gov), accession number D32046.

STEM CELL FACTOR: Williams, D. E., et al., *Cell*, 63:167–174 (1990). Copeland, N. G., et al., *Cell*, 63:174–183 (1990). Flanagan, J. G., et al., *Cell*, 63:185–194 (1990). Zsebo, K. M., et al., *Cell*, 63:213–224 (1990). Martin, F. H., et al., *Cell*, 63:203–211 (1990). Zsebo, K. M., et al., *Cell*, 63:195–201 (1990). Huang, E., et. al., *Cell*, 63:225–233 (1990). Anderson, D. M., et al., *Cell*, 63:235–243 (1990).

ONCOSTATIN M: Linsley, P. S., et al., *Mol. Cell. Biol.*, 10:1882–1890 (1990). Zarling, J. M., et al., *Proc. Natl. Acad. Sci. USA*, 83:9739–9743 (1986). Malik, N., et al., *Mol. Cell. Biol.*, 9:2847–2853 (1989).

AMPHIREGULIN: Plowman, G. D., et al., *Mol. Cell. Biol.*, 10:1969–1981 (1990). Shoyab, M., et al., *Proc. Natl. Acad. Sci. USA*, 85:6528–6532 (1988).

MULLERIAN-INHIBITING SUBSTANCE: Cate, R. L., et al., *Cell*, 45:685–698 (1986). Wallen, J. W., et al., *Cancer Res.*, 49:2005–2011 (1989). Picard, J-Y., et al., *Proc. Natl. Acad. Sci. USA*, 83:5464–5468 (1986). Coughlin, J. P., et al., *Mol. Cell. Endocrinol.*, 49:75–86 (1987).

B-CELL GROWTH FACTOR: Sharma, S., et al., *Science*, 235:1489–1492 (1987).

MACROPHAGE MIGRATION INHIBITORY FACTOR: Weiser, W. Y., et al., *Proc. Natl. Acad. Sci. USA*, 86:7522–7526 (1989).

ENDOSTATIN: O'Reilly, M. S., et al., *Cell*, 88:277–285 (1997).

ANGIOSTATIN: O'Reilly, M. S., et al., *Cell*, 79:315–328 (1994).

Also encompassed by the present invention are fusion proteins comprising biologically active fragments, analogs, mutants, variants or derivatives of the naturally-occurring proteins described herein. Biologically active fragments, derivatives, analogs, variants and mutants of the naturally-occurring proteins are also referred to herein as substantially similar proteins of the naturally-occurring protein. However, the level of biological activity of fragments, analogs, mutants, variants or derivatives of the naturally-occurring protein need not be identical to the activity of the naturally-occurring protein (also referred to herein as the parent protein). For example, a fragment of a cytokine protein may exhibit only 50–80% of the activity of the naturally-occurring cytokine, yet because two or more cytokines, either the same or different, are linked to form a fusion protein, the fusion protein exhibits increased biological activity as compared to a monomer of the naturally-occurring cytokine. Tests to determine biological activity are well-known to those of skill in the art and can include, for example, measuring the extent of hematopoiesis, platelet production or receptor binding. For example, the biological activity of a mutant of erythropoietin can be measured as described in U.S. Pat. Nos. 5,614,184 and 5,580,853, the teachings of which are herein incorporated by reference in their entirety.

The present invention also provides proteins with or without associated native-protein glycosylation. Expression of DNAs encoding the fusion proteins in bacteria such as *E. coli* provides non-glycosylated molecules. Functional mutant analogs having inactivated N-glycosylation sites can be produced by oligonucleotide synthesis and ligation or by site-specific mutagenesis techniques. These analog proteins can be produced in a homogeneous, reduced carbohydrate form in good yield using yeast expression systems. N-glycosylation sites in eukaryotic proteins are characterized by the amino acid triplet Asn-$A_1$-Z, where $A_1$ is any amino acid except Proline (Pro), and Z is Serine (Ser) or Threonine (Thr). In this sequence, asparagine provides a side chain amino group for covalent attachment of carbohydrate. Such a site can be eliminated by substituting another amino acid for Asparagine (Asn) or for residue Z, deleting Asparagine (Asn) or Z, or inserting a non-Z amino acid between $A_1$ and Z, or an amino acid other than Asparagine (Asn) between Asparagine (Asn) and $A_1$.

Derivatives and analogs can be obtained by mutations of the fusion protein. A derivative or analog, as referred to herein, is a polypeptide comprising an amino acid sequence that shares sequence identity, or similarity, with the full-length sequence of the wild type (or naturally occurring protein), except that the derivative or analog has one or more amino acid sequence differences attributable to a deletion, insertion and/or substitution.

Bioequivalent analogs of proteins can be constructed by, for example, making various substitutions of residues or sequences. For example, cysteine residues can be deleted or replaced with other amino acids to prevent formation of incorrect intramolecular disulfide bridges upon renaturation. Other approaches to mutagenesis involve modification of adjacent dibasic amino acid residues to enhance expression in yeast systems in which KEX2 protease activity is present. Generally, substitutions should be made conservatively; i.e., the most preferred substitute amino acids are those having physicochemical characteristics resembling those of the residue to be replaced. Similarly, when a deletion or insertion strategy is adopted, the potential effect of the deletion or insertion on biological activity should be considered. Due to degeneracy of the genetic code, there can be considerable variation in nucleotide sequences encoding the same amino acid sequence.

Mutations in nucleotide sequences constructed for expression of analogs must, of course, preserve the reading frame phase of the coding sequences and preferably will not create complementary regions that could hybridize to produce secondary mRNA structures such as loops or hairpins which would adversely affect translation of the mRNA. Alternatively, mutations could introduce secondary structure which would result in higher translational efficiency. Although a mutation site may be predetermined, it is not necessary that the nature of the mutation per se be predetermined. For example, in order to select for optimum characteristics of mutants at a given site, random mutagenesis may be conducted at the target codon and the expressed mutants screened for the desired activity.

Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures (see Example 5) can be employed to provide an altered gene having particular codons altered according to the substitution, deletion, or insertion required. Exemplary methods of making the alterations set forth above are disclosed by Walder et al. (*Gene* 42:133, 1986); Bauer et al. (*Gene* 37:73, 1985); Craik (*BioTechniques*, Jan. 12–19, 1985); Smith et al. (*"Genetic Engineering: Principles and Methods"*, Plenum Press, 1981); and U.S. Pat. Nos. 4,518,584 and 4,737,462 and are incorporated by reference herein.

In another embodiment, the fusion proteins described herein comprise variant type proteins produced by modifications in 5' and/or 3' noncoding regions of the wildtype gene. Hereinafter, the term recombinant variant protein will be used to describe these molecules.

These recombinant variant proteins can have altered biological activity. Each individual protein that comprises the fusion protein can itself have altered biological activity compared to the activity of the wildtype protein. Altered biological activity is defined herein as activity different from that of the wildtype or recombinant protein. For example, the activity of EPO is to regulate the growth and differentiation of red blood cell progenitors. Recombinant EPO variant proteins can have increased activity relative to wildtype EPO to regulate growth and differentiation of red blood cell progenitor cells. Alternatively, the EPO variant proteins can have decreased biological activity relative to the wildtype EPO.

Mutations in noncoding regions of the gene (e.g., 5' untranslated regions or UTR) can lead to differences in RNA translation as described, e.g., in Schultz, D. E., et al., *J. Virol.* 70:1041–1049, 1996; Kozak, M., *J. Mol. Biol.* 235:95–110, 1994; and Kozak, M., *J. Biol. Chem.* 266:19867–19870, 1991. For example, as described in detail in Example 4, computer modeling can be used to predict differences in RNA secondary structure (e.g., free energy of loops and base pairs) following nucleotide alterations in 3' and 5' UTR of the EPO gene. Although secondary structure changes in EPO RNA, following mutations in the 5' or 3' UTR, are used as the specific example, it is understood that the instant invention described herein can be used to produce any suitable polypeptide variant protein. As used herein, the term mutation refers to any alteration in the nucleic acid sequence encoding a polypeptide (e.g., a point mutation; the addition, deletion and/or substitution of one or more nucleotides).

Secondary structure has been shown to be a critical component in determining the rates of translation efficiency of several proteins (Bettany, A. J., et al., *J. Biol. Chem.* 267:16531–16537, 1992; Kozak, M., *J. Mol. Biol.* 235:95–110, 1994). By implication, altered rates of translation can affect posttranslational modifications, for example, glycosylation patterns, and, thus, proper folding of the resulting protein leading to changes in the chemistry, structure and function of the protein. The recombinant variant proteins described herein are unique in that they are composed of fusion proteins produced by mutations in 5' and 3' untranslated (noncoding) regions of the gene.

The present invention also provides recombinant expression vectors which include synthetic or cDNA-derived DNA fragments encoding fusion proteins comprising DNA encoding two or more linked proteins operably linked to suitable transcriptional or translational regulatory elements derived from mammalian, microbial, viral or insect genes. Such regulatory elements include a transcriptional promoter, an optional operator sequence to control transcription, a sequence encoding suitable mRNA ribosomal binding sites, and sequences which control the termination of transcription and translation, as described in detail below. The ability to replicate in a host, usually conferred by an origin of replication, and a selection gene to facilitate recognition of transformants may additionally be incorporated. Operably linked indicates that components are linked in such a manner that expression of the DNA encoding a fusion protein is controlled by the regulatory elements. Generally, operably linked means contiguous.

Transformed host cells are cells into which fusion protein vectors have been introduced by infectious or non-infectious methods. Transformed host cells ordinarily express the desired fusion protein, but host cells transformed for purposes of cloning or amplifying DNA do not need to express the protein. In eukaryotic cells, expressed fusion protein will generally be secreted into the culture supernatant. In prokaryotic cells, the fusion proteins may be expressed within the periplasmic space or as insoluble inclusion bodies. Suitable host cells for expression of fusion protein include prokaryotes, yeast or higher eukaryotic cells under the control of appropriate promoters. Prokaryotes include gram negative or gram positive organisms, for example *E. coli*. Higher eukaryotic cells include established cell lines of mammalian origin as described below. Cell-free translation systems could also be employed to produce fusion protein using RNAs derived from the DNA constructs of the present invention. Appropriate cloning and expression vectors for use with bacterial, fungal, yeast, and mammalian cellular hosts are described by Pouwels et al. ("*Cloning Vectors: A Laboratory Manual*", Elsevier, N.Y., 1985), which is incorporated herein by reference.

Prokaryotic expression vectors generally comprise one or more phenotypic selection markers, for example a gene encoding proteins conferring antibiotic resistance or supplying an autotrophic requirement, and an origin of replication recognized by the host to ensure amplification within the host. Suitable prokaryotic hosts for transformation include *E. coli, Bacillus subtilis, Salmonella typhimurium*, and various species within the genera Pseudomonas, Streptomyces, and Staphylococcus, although others may also be employed as a matter of choice.

Useful expression vectors for bacterial use can comprise a selectable marker and bacterial origin of replication derived from commercially available plasmids comprising genetic elements of the well-known cloning vector pBR322 (ATCC 37017). Such commercial vectors include, for example, pKK223-3 (Pharmacia Fine Chemicals, Uppsala, Sweden) and pGEM1 (Promega Biotech, Madison, Wis.). These pBR322 "backbone" sections are combined with an appropriate promoter and the structural sequence to be expressed. *E. coli* is typically transformed using derivatives of pBR322, a plasmid derived from an *E. coli* species (Bolivar et al., *Gene* 2:95, 1977). pBR322 contains genes for ampicillin and tetracycline resistance and thus provides simple means for identifying transformed cells.

Promoters commonly used in recombinant microbial expression vectors include the blactamase (penicillinase) and lactose promoter system (Chang et al., *Nature* 275:615, 1978; and Goeddel et al., *Nature* 281:544, 1979), the tryptophan (trp) promoter system (Goeddel et al., *Nucleic Acids Res.* 8:4057, 1980) and tac promoter (Sambrook, et al., "*Molecular Cloning: A Laboratory Manual*", 1989).

Recombinant fusion proteins may also be expressed in yeast hosts, preferably from the Saccharomyces species, such as *S. cerevisiae*. Yeast of other genera such as Pichia or Kluyveromyces may also be employed. Yeast vectors will generally contain an origin of replication from a yeast plasmid or an autonomously replicating sequence (ARS), promoter, DNA encoding the fusion protein, sequences for polyadenylation and transcription termination and a selection gene. Preferably, yeast vectors will include an origin of replication and selectable marker permitting transformation of both yeast and *E. coli*, e.g., the ampicillin resistance gene of *E. coli* and *S. cerevisiae* trp1 gene, which provides a selection marker for a mutant strain of yeast lacking the ability to grow in tryptophan, and a promoter derived from a highly expressed yeast gene to induce transcription of a structural sequence downstream. The presence of the trp1 lesion in the yeast host cell genome then provides an effective environment for detecting transformation by growth in the absence of tryptophan.

Suitable promoter sequences in yeast vectors include the promoters for metallothionein, 3-phosphoglycerate kinase (Hitzeman, et al., *J. Biol. Chem.* 255:2073, 1980) or other glycolytic enzymes (Hess, et al., *J. Adv. Enzyme Reg.* 7:149, 1968; and Holland, et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triose-phosphate isomerase, phosphoglucose isomerase, and glucokinase. Suitable vectors and promoters for use in yeast expression are further described in R. Hitzeman, et al., EPA 73,657.

Preferred yeast vectors can be assembled using DNA sequences from pBR322 for selection and replication in *E. coli* (Amp gene and origin of replication) and yeast DNA sequences including a glucose-repressible ADH2 promoter and α-factor leader, which directs secretion of heterologous proteins, can be inserted between the promoter and the structural gene to be expressed (Kurjan, et al., *Cell* 30:933, 1982; and Bitter, et al., *Proc. Natl. Acad. Sci. USA* 81:5330, 1984). The leader sequence may be modified to contain, near its 3' end, one or more useful restriction sites to facilitate fusion of the leader sequence to foreign genes.

Suitable yeast transformation protocols are known to those of skill in the art; an exemplary technique is described by Hinnen, et al., *Proc. Natl. Acad. Sci. USA* 75:1929, 1978, selecting for Trp$^+$ transformants in a selective medium consisting of 0.67% yeast nitrogen base, 0.5% casamino acids, 2% glucose, 10 µg/ml adenine and 20 µg/ml uracil.

Host strains transformed by vectors comprising the ADH2 promoter may be grown for expression in a rich medium consisting of 1% yeast extract 2% peptone, and 1 glucose supplemented with 80 µg/ml adenine and 80 µg/ml uracil. Derepression of the ADH2 promoter occurs upon exhaustion of medium glucose. Crude yeast supernatants are harvested by filtration and held at 4° C. prior to further purification. Various mammalian or insect cell culture systems can be employed to express recombinant protein. Baculovirus systems for production of heterologous proteins in insect cells are reviewed by Luckow and Summers, *Bio/Technology* 6:47, 1988.

Examples of suitable mammalian host cell lines include the COS-7 lines of monkey kidney cells, described by Gluzman (*Cell* 23:175, 1981), and other cell lines capable of expressing an appropriate vector including, for example, L cells, C127, 3T3, Chinese Hamster Ovary (CHO), HeLa and BHK cell lines. Mammalian expression vectors may comprise non-transcribed elements such as an origin of replication, a suitable promoter and enhancer linked to the gene to be expressed, and other 5' or 3' flanking nontranscribed sequences, and 5' to 3' nontranslated sequences, such as necessary ribosome binding sites, a poly-adenylation site, splice donor and acceptor sites, and transcriptional termination sequences.

The variant nucleic acid molecules encoding, for example, recombinant polypeptide variant proteins created by modifying the 3' and/or 5' UTR of the polypeptide gene, would also preferably contain regulatory sequences. Regulatory sequences include all cis-acting elements that control transcription and regulation such as, promoter sequences, enhancers, ribosomal binding sites, and transcription binding sites. Selection of the promoter will generally depend upon the desired route for expressing the protein. For example, where the protein is to be expressed in a recombinant eukaryotic or prokaryotic cell, the selected promoter is recognized by the host cell. A suitable promoter which can be used can include the native promoter for the binding moiety which appears first in the construct.

The elements which comprise the nucleic acid molecule can be isolated from nature, modified from native sequences or manufactured de novo, as described, for example, in the above-referenced texts. The elements can then be isolated and fused together by methods known in the art, such as exploiting and manufacturing compatible cloning or restriction sites.

The nucleic acid molecules can be inserted into a construct which can, optionally, replicate and/or integrate into a recombinant host cell, by known methods which may vary depending upon the form of the recombinant polypeptide which is expressed. The host cell can be a eukaryotic or prokaryotic cell and includes, for example, pichia expression systems, yeast (such as, Saccharomyces), bacteria (such as, Escherichia or Bacillus), animal cells or tissue, including insect (such as, Spodoptera frugiperda 9 or mammalian cells (such as, somatic or embryonic human cells, Chinese hamster ovary cells, HeLa cells, human 293 cells, monkey kidney COS-7 cells, baby hamster kidney BHK cells, C127 cells, etc.). The selection of the host cell governs the posttranslational modifications that may occur. For instance, glycoproteins could be expressed in mammalian, insect, or yeast cells whereas nonglycosylated proteins could be expressed in bacteria. In addition, the selection of the appropriate host cell may differ when expressing recombinant polypeptide variants manufactured by mutations in the noncoding regions of the gene. (Schultz, et al., *J. Virol.* 70:1041–1049, 1996).

The nucleic acid molecule can be incorporated or inserted into the host cell by known methods. Examples of suitable methods of transfecting or transforming cells include calcium phosphate precipitation, electroporation, microinjection, infection, lipofection and direct uptake. Methods for preparing such recombinant host cells are described in more detail in several technical books, for example, Sambrook, et al., "Molecular Cloning: A Laboratory Manual," (1989) and Ausubel, et al. "Current Protocols in Molecular Biology," (1995).

The host cells are then maintained under suitable conditions for expressing and recovering the recombinant polypeptide. Generally, the cells are maintained in a suitable buffer and/or growth medium or nutrient source for growth of the cells and expression of the gene product(s). The growth media are generally known in the art and include sources of carbon, nitrogen and sulfur. Examples include Dulbeccos modified Eagles media (DMEM), RPMI-1640, M199 and Grace's insect media. The selection of a buffer is not critical to the invention. The pH which can be selected is generally one tolerated by or optimal for growth for the host cell.

The cell is maintained under a suitable temperature and atmosphere. For example, an aerobic host cell is maintained under aerobic atmospheric conditions or other suitable conditions for growth. The temperature should also be selected so that the host cell tolerates the process and can be, for example, between about 27° C. and 40° C.

The transcriptional and translational control sequences in expression vectors to be used in transforming vertebrate cells may be provided by viral sources. For example, commonly used promoters and enhancers are derived from Polyoma, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide the other genetic elements required for expression of a heterologous DNA sequence. The early and late promoters are particularly useful because both are obtained easily from the virus as a fragment which also contains the SV40 viral origin or replication (Fiers, et al., *Nature* 273:113, 1978). Smaller or larger SV40 fragments may also be used, provided the approximately 250 bp sequence extending from the Hind III site toward the BgII site located in the viral origin or replication is included. Exemplary vectors can be constructed as disclosed by Okayama and Berg (*Mol. Cell. Biol.* 3:280, 1983).

Preferred eukaryotic vectors for expression of mammalian DNA include pIXY321 and pIXY344, both of which are yeast expression vectors derived from pBC102.K22(ATCC 67,255) and contain DNA sequences from pBR322 for selection and replication in *E. coli* (Apr gene and origin of replication) and yeast.

Purified mammalian fusion proteins or analogs are prepared by culturing suitable host/vector systems to express the recombinant translation products of the DNAs of the present invention, which are then purified from culture media or cell extracts. For example, supernatants from systems which secrete recombinant protein into culture media can be first concentrated using a commercially available protein concentration filter, for example, an Amicon or Millipore Pellicon ultrafiltration unit. Following the concentration step, the concentrate can be applied to a suitable purification matrix.

The recombinant molecules produced by the processes described herein, including those manufactured by modifications in the 3' and 5' UTR, can be isolated and purified by known means. Examples of suitable purification and isolation processes are generally known in the art and include, but are not limited to, ammonium sulfate precipitation, dialysis, electrophoresis, ultrafiltration, microfiltration, gel filtration, ion exchange or immunoaffinity chromatography. In addition, one or more reverse phase high performance liquid chromatography (RP-HPLC) media, e.g., silica gel having pendant methyl or other aliphatic groups, can be employed to further purify a fusion protein composition. Some or all of the foregoing purification steps, in various combinations, can also be employed to provide a homogenous recombinant protein.

Recombinant protein produced in bacterial culture is usually isolated by initial extraction from cell pellets, followed by one or more concentration, salting-out, aqueous ion exchange or size exclusion chromatography steps. Finally, high performance liquid chromatography (HPLC) can be employed for final purification steps. Microbial cells employed in expression of recombinant fusion proteins can be disrupted by any convenient method, including freeze-thaw cycling, sonication, mechanical disruption, or use of cell lysing agents.

Fermentation of yeast which express fusion proteins as a secreted protein greatly simplifies purification. Secreted recombinant protein resulting from a large scale fermentation can be purified by methods analogous to those disclosed by Urdal, et al., (*J. Chromatog.* 296:171, 1984).

Fusion protein synthesized in recombinant culture is characterized by the presence of non-human cell components, including proteins, in amount and of a character which depend upon the purification steps taken to recover the fusion protein from the culture. These components ordinarily will be of yeast, prokaryotic or non-human higher eukaryotic origin and preferably are present in innocuous contaminant quantities, on the order of less than about 5 percent by scanning densitometry or chromatography. Further, recombinant cell culture enables the production of the fusion protein free of proteins which may be normally associated with EPO as they are found in nature in their respective species of origin, e.g., in cells, cell exudates or body fluids.

The present invention further relates to pharmaceutical compositions comprising a fusion protein and a physiologically-compatible carrier. Such carriers are described in U.S. Pat. No. 5,580,853, the teachings of which are herein incorporated by reference in their entirety. Pharmaceutical compositions suitable for administration comprise the fusion protein in an effective amount and a physiologically acceptable carrier. An effective amount, as used herein, is defined as that quantity which alleviates, to any degree, or eliminates the condition for which the mammal is being treated.

The carriers will be non-toxic to recipients at the dosages and concentrations employed. The formulation used will vary according to the route of administration selected (e.g., solution, emulsion, capsule). For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. Intravenous vehicles can include various additives, preservatives, or fluid, nutrient or electrolyte replenishers. See, generally, *"Remington's Pharmaceutical Science"*, 16th Edition, Mack, Ed. (1980). For inhalation, the compound can be solubilized and loaded into a suitable dispenser for administration (e.g., an atomizer, nebulizer or pressurized aerosol dispenser). Fusion proteins can be administered individually, together or in combination with other drugs or agents (e.g., other chemotherapeutic agents, immune system enhancers).

Fusion protein compositions can be used to enhance proliferation, differentiation and functional activation of hematopoietic progenitor cells, such as bone marrow cells. Fusion protein compositions can also be used in the treatment of cancers or cellular growth deficiencies. Specifically, compositions containing the fusion protein may be used to increase peripheral blood leukocyte numbers and increase circulating granulocyte counts in myelosuppressed patients. To achieve this result, a therapeutically effective quantity of a fusion protein composition is administered to a mammal, preferably a human, in association with a pharmaceutical carrier or diluent.

The recombinant polypeptide variant proteins of the invention can be used as therapeutic for delivery to individuals having diseases or conditions that are associated with deficiencies or abnormalties of the proteins described herein. The retention and/or deletion of nucleotides in untranslated regions of the polypeptide gene can produce heterologous therapeutic proteins. Heterologous proteins are herein defined as proteins which does not exist in nature and exhibit a range of therapeutic effects.

Recombinant polypeptides with therapeutic value are known in the art. Examples include the recombinant EPO described in Lin (U.S. Pat. No. 4,703,008); Sytkowski and Grodberg (U.S. Pat. No. 5,614,184); Sytkowski (U.S. Pat. No. 5,580,853); and Powell (U.S. Pat. No. 5,688,679); the contents of which are incorporated herein by reference.

For example, the recombinant EPO variant proteins described herein can be employed in any method where EPO would be effective, and in particular in methods where other man-made EPO proteins have not produced any clinically beneficial effect (e.g., increasing red blood cells in an anemic patient). The mode of EPO administration to patients is preferably at the location of the target cells. As such, the administration can be by injection. Other modes of administration (parenteral, mucosal, systemic, implant, intraperitoneal, etc.) are generally known in the art and, for EPO, can be determined, for example, as described in U.S. Pat. No. 5,614,184. The recombinant EPO proteins can, preferably, be administered in a pharmaceutically acceptable carrier, such as saline, sterile water, Ringer's solution, and isotonic sodium chloride solution.

The activity of polypeptide variant proteins can be tested, for example, in pharmacological differences. Accordingly, the activity of the recombinant EPOs could be evaluated therapeutically. For example, pharmacological differences in the secreted and purified EPO manufactured by the disclosed method compared to other man-made or naturally occurring EPOs can include:

1. An increase or decrease in the potency when administered to patients in human clinical trials. The difference can be in the required initial dose as well as maintenance doses. A relative potency factor can be evaluated for the recombinant EPO variant proteins.
2. A reduction or increase in potential side effects in patients may reflect altered activities of the EPO variant proteins. For example, differences can be manifested as an increase or decrease in blood pressure which can be of extraordinary significance in designing treatment regimens for certain high risk patients like dialysis patients who are, in any case, severely ill.
3. A difference in the time lag between the effect of increasing red blood cells in the patient's serum after administration of the EPO variants. This time-lag has the consequence that the desired therapeutic effect is either accelerated or delayed significantly compared to other forms of recombinant EPO. A decrease in the time lag would be a desirable therapeutic effect by resulting in a faster benefit to the patient.
4. The ability of a patient to tolerate one form of EPO and not another. If a patient can not tolerate one form of an EPO variant over another, this noncompatibility can indicate therapeutic differences which in turn can reflect structural, biochemical and biological modifications in the various forms of recombinant EPO.
5. An increase in the circulating half-life of EPO in patients which can result in less frequent injections or smaller doses of EPO having to be administered. A prolonged half-life would not only be therapeutically beneficial, but also diminish health care costs in the treatment of chronically ill patients.

Thus, differences in the pharmaceutical characteristics of recombinant polypeptide variant proteins can result in variations in therapeutic effects (e.g., for EPO variants, the production of reticulocytes and red blood cells and an increase in hemoglobin synthesis and iron uptake). For example, a difference in the inherent potency which would result in lower bioloads inflicted on the patient's body by administering an EPO protein which leads to an absence or drastic lowering of side effects (which may endanger the patient's life or make it impossible to administer one form of EPO) is particularly important in high risk patients (e.g., patients with kidney disorders) who are at high risk for hypertension, myocardial infarct or stroke.

Thus, retention, deletion, point mutation or substitution in the 5' and/or 3' UTR sequences of a recombinant EPO gene fragment can ultimately influence the final structure and chemistry of a protein expressed by a host cell transfected with that gene fragment. As a consequence the resulting expressed protein can exhibit varying biological parameters which can be assessed using bioassays and in therapeutics.

The present invention will now be further illustrated by the following exemplification, which is not meant to be limiting in any way.

EXAMPLE 1

CONSTRUCTION OF THE EPO—EPO DIMER

Figure 2:
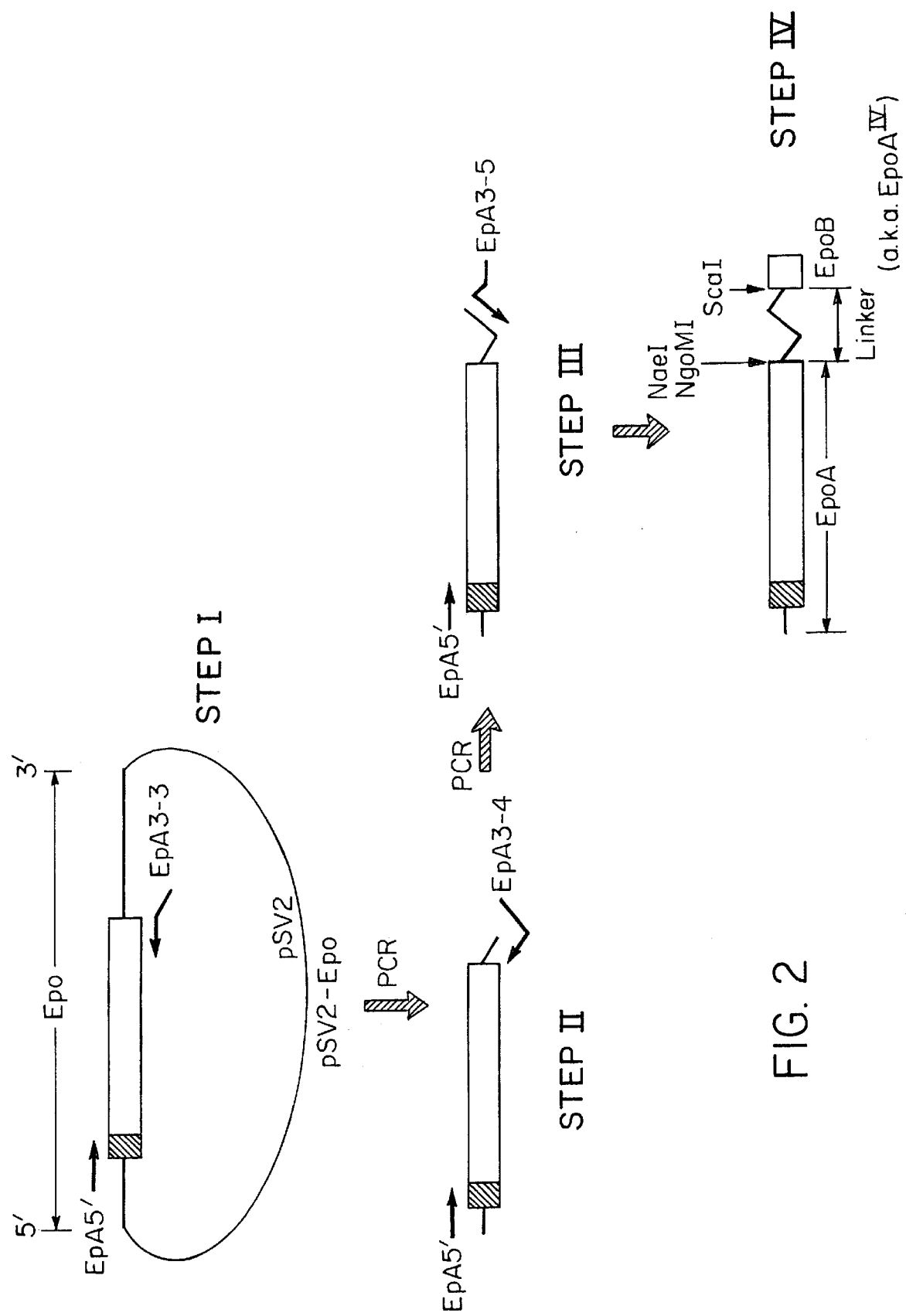
FIG. 2 is a diagram showing production of EPO A DNA and sequential elongation of linking DNA strand encoding [gly-gly-gly-gly-ser]$_3$ using PCR.
Figure 4:
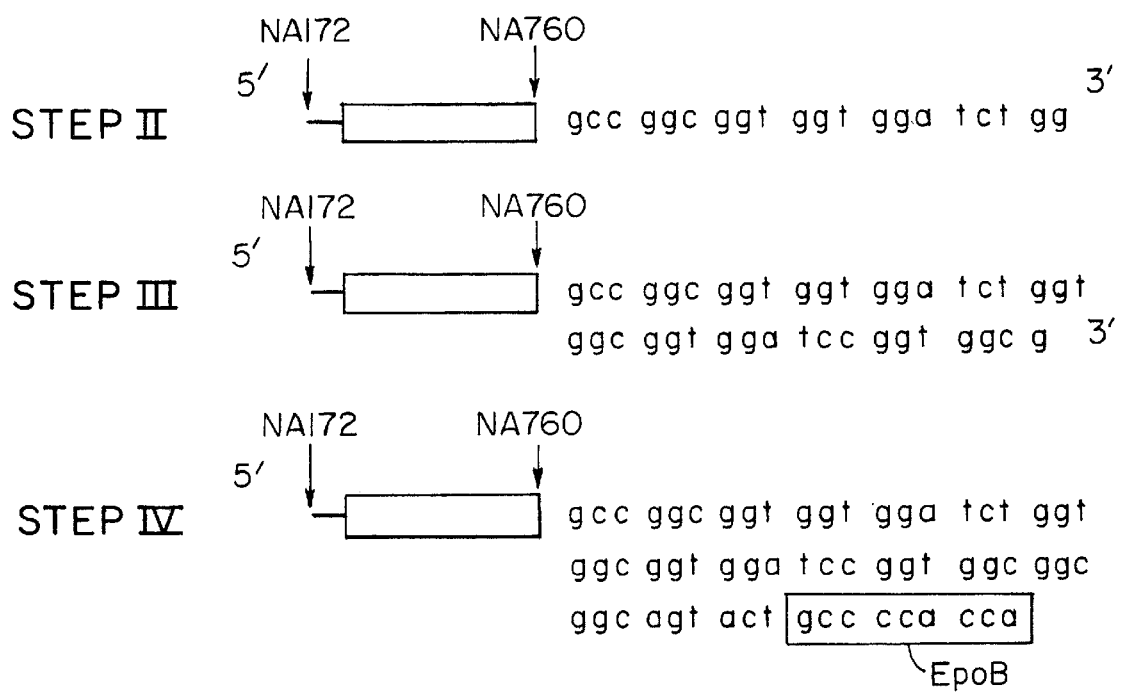
FIG. 4 is a diagram showing the end product of each of steps II–IV of FIG. 2.
Figure 5:
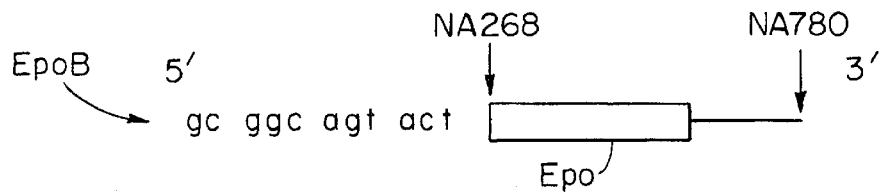
FIG. 5 is a diagram showing the end product of FIG. 3.

An EPO—EPO fusion protein was constructed by linking two strands of EPO cDNA with a DNA strand encoding the following polypeptide: AGGGGSGGGGSGGGGST (SEQ ID NO: 13) (FIG. 1). The nucleotide sequence of wild type erythropoietin can be obtained from Jacobs, K., et al., Nature 323:806, 1985, which is herein incorporated by reference in its entirety. The linking DNA strand was sequentially lengthened to the proposed length by using psv2-EPO (FIG. 2) as template and 3' primers with appropriately extended 3' ends (FIG. 2). The initial preceding EPO DNA strand (FIG. 4) contains 10 nucleotides in the 5' untranslated region, a leader sequence (Jacobs, K., et al., Nature 323:806, 1985), an EPO cDNA coding sequence, and no STOP codon. Additional nucleotides attached to the 3' end were: GCCGGCGGTG-GTGGATCTGG (SEQ ID NO: 14). The EPO DNA strand after the linker (EPO B DNA; FIG. 5) contains no leader sequence but has a STOP codon and 17 nucleotides in the 3' untranslated region. Half a NaeI restriction site was designed into the 3' end of EPO A DNA and half a ScaI restriction site into the 5' end of EPO B DNA.

Figure 3:
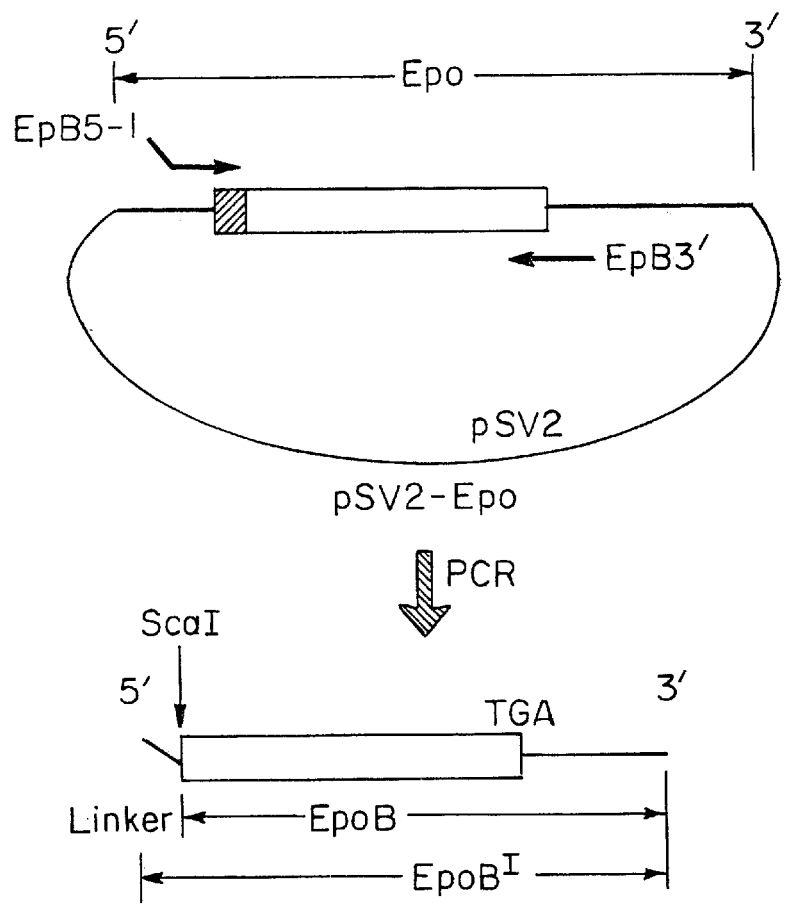
FIG. 3 is a diagram showing production of EPO B DNA using PCR.

EPO A (FIG. 2) and EPO B (FIG. 3) DNA were produced by the using the Polymerase Chain Reaction (PCR) and a human EPO cDNA plasmid, psv2-EPO (Chern, Y. J., et al., Eur J Biochem 202:225, 1991) as template.

Primers used to produce EPO A are as follows: 5'-AGGCGCGGAGATGGGGGTGCAC (SEQ ID NO: 15) (EpA 5'), 3'-CCAGATCCACCACCGCCGGCTCTGTCCCCTGTCC TGCAGG (SEQ ID NO: 16) (EpA3-3), 3'-CGCCACCGGATCCACCGCCACCAGATCCACCACC GCCGGC (SEQ ID NO: 17) (EpA3-4), and 3'-TGGTGGGGCAGTACTGCCGCCGCCACCGGATCCA CCGCC (SEQ ID NO: 18) (EpA3-5).

Primers used to produce EPO B are as follows: 5'-GCGGCAGTACTGCCCCACCACGCCTCATCTGTGA CAGC (SEQ ID NO: 19) (EpB 5-1) and 3'-CAGGTGGACACACCTGGTCATC (SEQ ID NO: 20) (EpB 3').

PCR reactions (50 µl) contained the following components: 0.5 µM of 5' primer or 3' primer; 10 ng psv2-EPO; 200 µM of DATP, dCTP, dGTP, or dTTP; 20 mM Tris-HCl (pH 8.0); 2 mM $MgCl_2$; 10 mM KCl; 6 mM $(NH_4)_2SO_4$; 0.1% Triton X-100; 10 µg/ml nuclease-free BSA; and 2.5 U Pfu DNA Polymerase (Stratagene). The reactions were overlaid with mineral oil (50 µl; Molecular Biology Grade, Sigma) and subjected to 25 cycles of 94° C. for 1 min (denaturation), of 52° C. for 1 min (annealing) and of 72° C. for 1 min (extension) in a Perkin Elmer DNA Thermal Cycler 480.

Next, the DNA sequences of the PCR products were determined. First, the PCR products were purified from a 1% agarose gel using the QIAQUICK™ Gel Extraction Kit. They were then ligated to pCR-blunt, in which the reactions contained an insert to vector molar ratio of 10 to 1. The ligation reactions (10 µl) contained the gel-purified PCR products, 25 ng of PCR-blunt, 1× ligation buffer and 4 U of T4 DNA ligase (ZERO BLUNT™ PCR Cloning Kit, Invitrogen). Incubations were carried out for 1 hour at 16° C.

Cells used for expression were TOP 10™ Competent Cells (Invitrogen) and were transformed according to procedure established by Invitrogen: 2 µl of β-mercaptoethanol was added to the cells on ice, mixed by gentle swirling with a pipette tip, followed by 2 µl of the ligation described in the preceding paragraph. This mixture was then incubated on ice for 30 min, followed by exactly 45 seconds at 42° C. The vial was then placed on ice for 2 min. Pre-warmed (37° C.) SOC medium (250 µl) containing 2% tryptone, 0.5 yeast extract, 10 mM NaCl, 2.5 mM KCl, 10 mM $MgCl_2$, 10 mM $MgSO_4$, and 20 mM glucose was added and the cells shaken for 1 hr at 37° C. Fifty µl of a 1:5 dilution of transformed cells were plated on LB (Miller's modification, Sigma) agar plates containing 50 µg/ml kanamycin. The plates were incubated at 37° C. overnight. Colonies were plucked and 2.5 ml LB containing 50 µg/ml kanamycin were inoculated with these colonies. Plasmid DNA were prepared from the overnight cultures using Promega's WIZARD PLUS MINI-PREPS™ DNA Purification System. Clones were analyzed by restriction digest fragment analysis.

The pCRBlunt-EPO A and pCRBlunt-EPO B DNA clones were digested with BglI, which gave unique-sized fragments for a correctly inserted DNA and an insert oriented in the reverse direction (FIGS. 6 and 7). Clones with inserts in the reverse direction were chosen and larger amounts (from 100 ml of LB/50 µg/ml kanamycin) of DNA plasmids prepared using Promega's WIZARD PLUS MAXIPREPS™ DNA purification system. Clones with inserts in the "forward" direction would also have produced the proposed EPO—EPO DNA.

Figure 11:
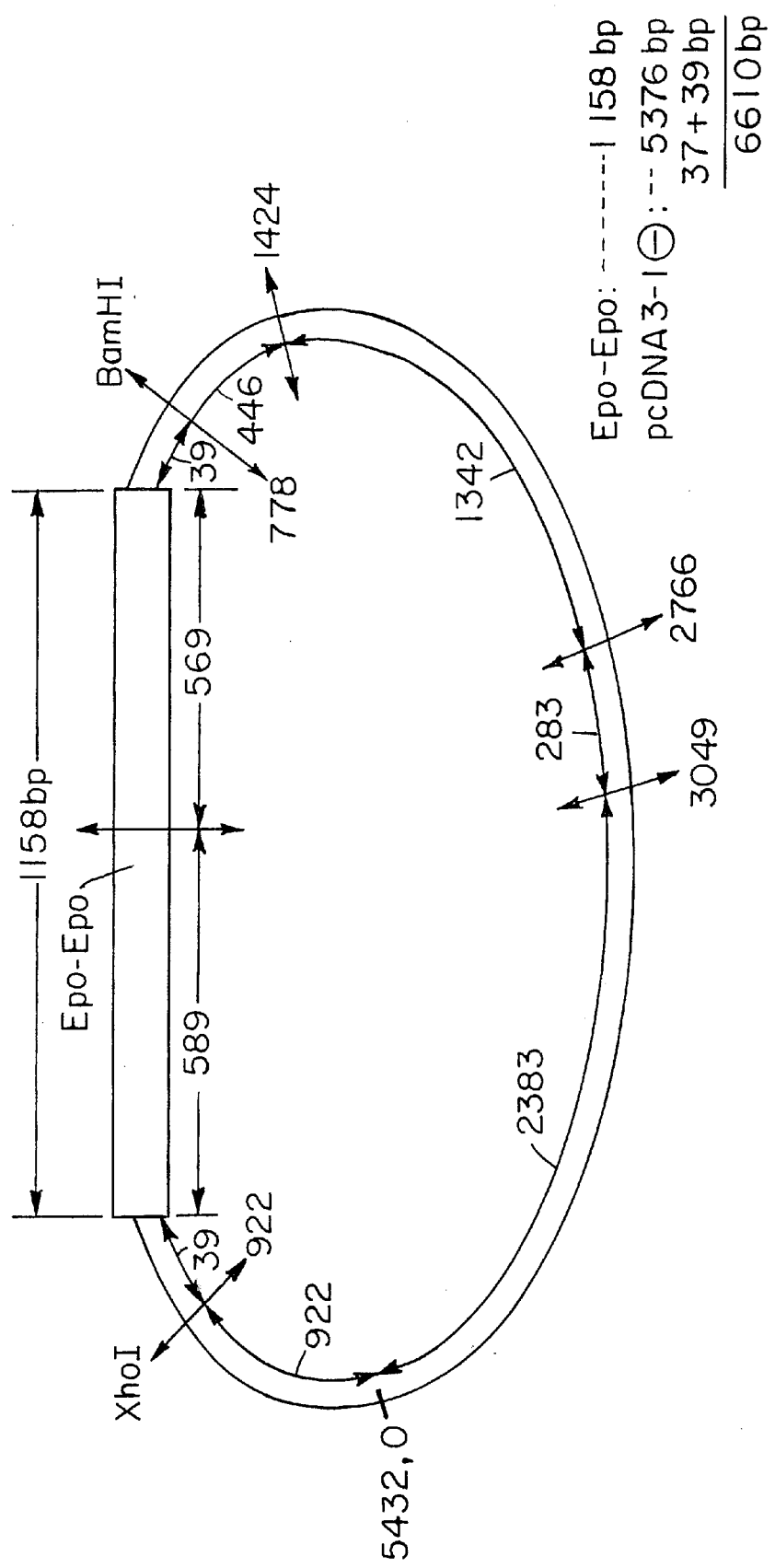
FIG. 11 is a diagram showing the restriction digest of pcDNA3.1-EPO—EPO.

EPO A DNA was linked to EPO B DNA using the procedure described as follows. pCRBlunt-EPO A(−) was digested with Sca I and Xho I and the 677 bp fragment gel purified (FIG. 8). pCRBlunt-EPO B(−) was digested with BamHI and ScaI and the 557 bp fragment gel purified (FIG. 9). The EPO A 677 bp fragment was then ligated to the EPO B 557 bp fragment in a 1:1 molar ratio of EPO A 677 bp fragment to EPO B 557 bp fragment. Ligations were carried out overnight at 16° C. The ligated EPO A/EPO B DNA fragments were purified using QIAQUICK™ Gel Extraction Kit then ligated to pcDNA2.1(−) which had previously been digested with XhoI and BamHI and gel purified (FIG. 10). The ligation reaction contained a 5:1 molar ratio of DNA insert to pcDNA3.1(−). The incubation was carried out overnight at 16° C. Clones were picked from ampicillin-resistant colonies by restriction digest analysis (FIG. 11), produced in microgram quantities, and used to transfect COS I cells.

EXAMPLE 2

TRANSIENT EXPRESSION OF EPO DIMER IN COS I CELLS

COS I cells were grown to 70% confluency in Dulbecco's Modified Eagle Medium, high glucose (4.5 g/L; Gibco), 10% fetal bovine serum (Hyclone) in the presence of 100 U penicillin, 100 µg streptomycin, 250 ng Fungizone per ml of tissue culture medium (antibiotic-antimycotic cocktail from Gibco) at 37° C. and 10% $CO_2$. The cells were harvested by trypsinizing using 0,05% Trypsin, 0.53 mM EDTA (Gibco) and washing twice with phosphate buffered saline (PBS)/6 mM glucose solution. Cells were suspended in the above PBS/glucose buffer to a concentration of $2\times10^6$ cells/ml. 0.5 ml of cells were placed in electroporation cuvettes (0.4 cm gap, BiV-Rad) and 10 µg of pcDNA/EPO-EPO added. The cells were electroporated under the following conditions: voltage=0.3 kV, field strength=0.75 kV/cm, capacitor=250 µF, and resistor=none (Pulse controller set at Ω). Cells were plated in 30 ml of pre-warmed DMEM, high glucose, 10% pBS and incubated for 72 h at 37° C. and 10% $CO_2$. The controls used were 10 µg of pcDNA-EPO and 10 µg of pcDNA 3.1(−).

The conditioned media were collected, centrifuged at 13,800×g for 10 min at 4° C. Aliquots (1 ml) of each conditioned media were dialyzed against Minimum Essential Medium a overnight with 3 changes of medium. These samples were assayed for EPO activity by the method of Krystal as described in U.S. Pat. No. 5,580,853, which is herein incorporated by reference in its entirety. The conditioned medium of cells transfected with pcDNA/EPO—EPO was 45–72 U/ml in an in vitro bioassay, and the medium from cells transfected with pcDNA-EPO was 5 U/ml. Conditioned media from cells transfected with pcDNA and untransfected cells showed no EPO activity.

EXAMPLE 3

IN VIVO ACTIVITY OF pcDNA/EPO—EPO

Conditioned medium from cells transfected with pcDNA/EPO—EPO was used to inject mice (B6C3F1 strain, female, 18 g, Jackson Labs). The haematocrits of these mice were measured prior to administering EPO—EPO. 300 U Mouse were injected subcutaneously (EPO—EPO 300 IU per kg) on day 1, day 3, and day 5. Haematocrits were determined measured on day 7. Mouse #1 showed an increase haematocrit of 4.5% and mouse #2 an increase of 1.5%.

A more extensive study was subsequently conducted with four mice in a control group and four mice in an experimental group (B6C3F1 strain, female, 18 g, Jackson Labs). The control group was treated with 200 µl of medium on day 1, day 3, and day 5, while the experimental group was treated with 300 U/kg of fusion protein pcDNA/EPO—EPO in 200 µl of medium on day 1 only. The haematocrits of all mice in the study were measured prior to administration (day 0) and following administration (day 8).

The results are summarized in Table 1 and Table 2 below. The mean increase for the experimental group from 46.2 on day 0 to 48.8 on day 8 represents the equivalent of one unit of blood.

TABLE 1

HEMATOCRITS OF CONTROL GROUP

| Mouse No. | Day 0 | Day 8 |
|---|---|---|
| 1 | 47.5 | 48.0 |
| 2 | 50.0 | 48.0 |
| 3 | 46.5 | 47.5 |
| 4 | 46.0 | 45.0 |
| Mean | 47.5 | 47.0 |

TABLE 2

HEMATOCRITS OF EXPERIMENTAL GROUP

| Mouse No. | Day 0 | Day 8 |
|---|---|---|
| 1 | 48.5 | 50.5 |
| 2 | 47.0 | 50.0 |
| 3 | 45.0 | 47.0 |
| 4 | 44.0 | 48.0 |
| Mean | 46.0 | 49.0 |

EXAMPLE 4

POLYPEPTIDE VARIANTS PRODUCED BY ALTERING NONCODING REGIONS OF THE GENE

Typically, variants of recombinant proteins are made by deleting, adding or substituting nucleotides within the coding of the gene. However, it is also possible to make variants of recombinant proteins by altering the noncoding regions of genes, i.e., the 5' and 3' untranslated regions (UTR). Modifications in the UTR of a gene, especially in the 5' sequence as well as in the first intron, influence the regulation of translation; and, thus, the expression of proteins (Schultz, D. E., et al., *J. Virol.* 70:1041–1049, 1996; Kozak, M., *J. Mol. Biol.* 235:95–110, 1994; Bettany, A. J., et al., *J. Biol. Chem.* 267:16531–16537, 1992; Kozak, M., *J. Biol. Chem.* 266:19867–19870, 1991).

Alterations in the non-coding sequences of a polypeptide gene can result in different mRNA secondary structure (e.g., free energy of the loops and base pairs), translation efficiency; and subsequently, the expression, secretion and biological activity of the polypeptide. Therefore, different forms of polypeptides can be manufactured as a result of modifications in regions which flank either the 5' or 3' side of the coding region of a polypeptide.

Figure 12:
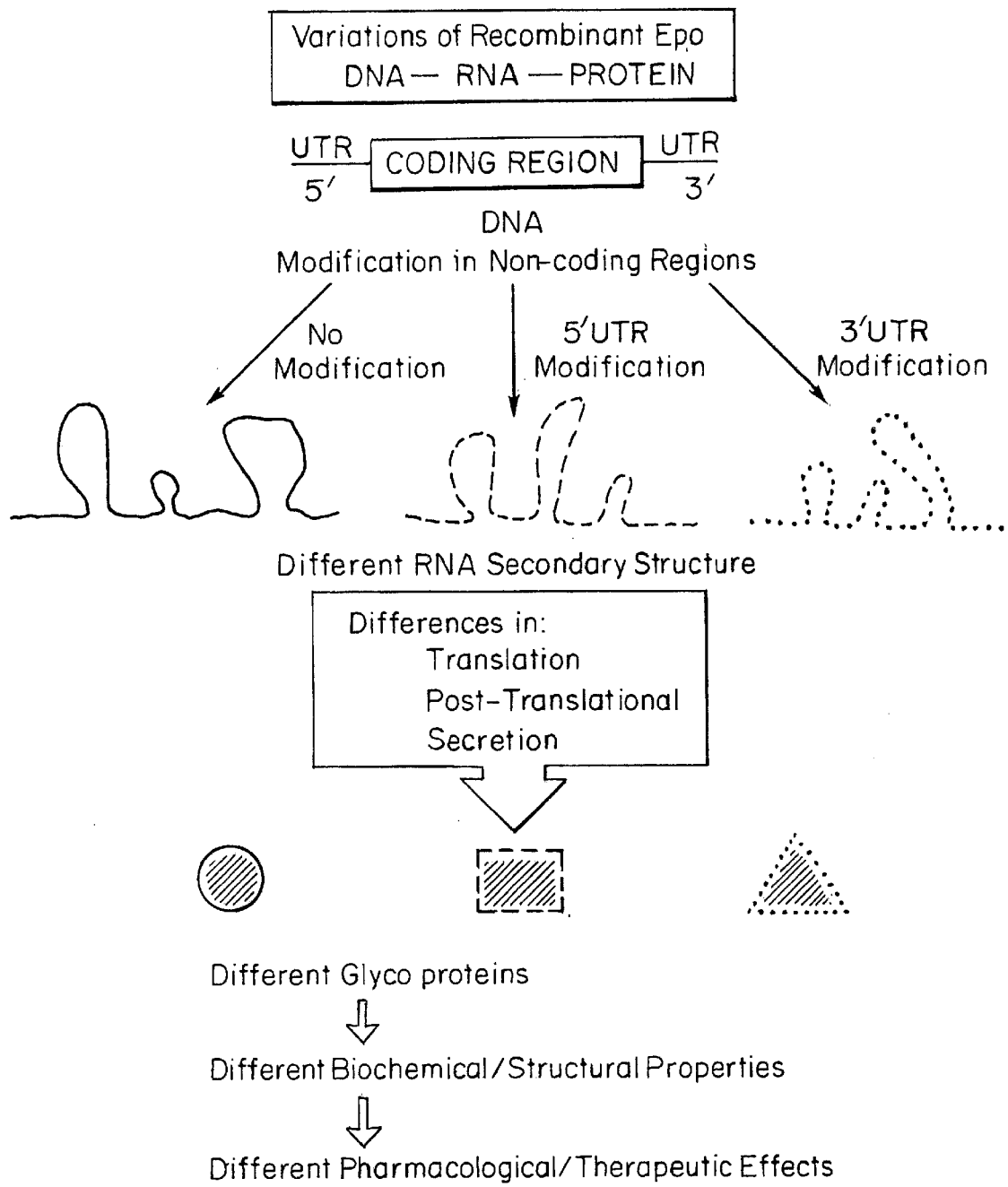
FIG. 12 is a schematic representation describing how differences in mRNA and protein structure; and protein function can result from alterations in the 5' and 3' UTR of a gene.

FIG. 12 is a schematic representation of changes in mRNA structure and ultimately protein structure and function that can result when an alteration(s) is made in the 5' and/or 3' UTR of the recombinant polypeptide gene. Variations in the recombinant polypeptide can be produced as, for example, different restriction enzyme generated fragments of genomic sequences and/or specific nucleotide substitutions and mutations in the 5' and/or 3' UTR of the polypeptide coding sequence. Oligonucleotide-directed site-specific mutagenesis procedures as described herein can be employed to provide the recombinant polypeptide variant proteins.

Modifications in the noncoding regions of the polypeptide gene can affect mRNA stability, rates of translation, expression from host cells, protein processing, export from rough endoplasmic reticulum, extent and pattern of glycosylation, secretion dynamics and rates of export from the cell. For example, varied glycosylation patterns can result, which, for EPO, are of great importance for biological activity (Yamaguchi, K., et al., *J. Biol. Chem.* 266:20434–20439, 1991). The resulting proteins can represent chemically, structurally and biologically distinct forms of recombinant polypeptides.

The nucleotide sequences of polypeptide variants can be confirmed by DNA sequencing using standard experimental procedures. Distinctive versions of genomic polypeptides can be produced by mutations in the 5' and 3' UTR and can be detected by Southern blotting. Likewise, different mRNAs can be identified by Northern blotting. Differences in hybridization conditions, i.e., high or low stringencies, will be an index of the diversity of the DNA and mRNA. It is possible that different genomic sequences may require different promoters (e.g., mouse metallothionein or 3-phosphoglycerate), vectors (e.g., bovine papilloma virus), and/or host cells (e.g., CHO, BHK-21 or C127 cells) to adequately express the recombinant polypeptide. The technical methods which can be employed for the above mentioned experimental strategies are familiar to those of skill in the art. For example, detailed protocols can be found in Sambrook, et al., "*Molecular Cloning: A Laboratory Manual*," (1989) and Ausubel, et al., "*Current Protocols in Molecular Biology,*" (1995); Powell, J. S., et al., *Proc. Natl. Acad. Sci. USA* 83:6465–6469, 1986; and Sytkowski and Grodberg, (U.S. Pat. No. 5,614,184); Sytkowski (U.S. Pat. No. 5,580,853); and Powell (U.S. Pat. No. 5,688,679); the teachings of which are herein incorporated by reference in their entirety.

Mutations in the 5' and/or 3' UTR of the polypeptide gene can result in altered RNA structure, total free energy, stability and/or rates and efficiency of translation (Schultz, D. E., et al., *J. Virol.* 70:1041–1049, 1996; Kozak, M., *J. Mol. Biol.* 235:95–110, 1994; Bettany, A. J., et al., *J. Biol. Chem.* 267:16531–16537, 1992; Kozak, M., *J. Biol. Chem.* 266:19867–19870, 1991; Purvis, I. J., et al., *Nucleic Acids Res.* 15: 7951–62, 1987). The secondary structure of mRNAs play an important role in the initiation and efficiency of translation and, thus, in protein synthesis.

Computer modeling using the PC/Gene® RNAFOLD program (IntelliGenetics, Inc.) is used to predict differences in RNA secondary structure, specifically the total free energy, following deletion in the 5' or 3' UTR of, for example, the EPO gene (FIGS. 13–15). The program utilizes an algorithm which calculates the energies of the secondary structure of RNA. It automatically transcribes any DNA sequence into a single stranded RNA sequence. Since the mRNA is single stranded, it can fold back upon itself due to the complementarity of bases resulting in various "loops". Energy must be released to form a base-paired or looped structure and the stability of the resulting secondary structure is determined by the amount of energy released. Therefore, if alternative structures have a free energy of formation of −50 kcal/mol and −100 kcal/mol, the latter structure is intrinsically more likely to be formed.

For example, free energy for the secondary RNA structure for nucleotides 401–624 in the 5' UTR of the EPO gene is predicted to be −161.0 kcal/mol (SEQ ID NO:2). A 50 nucleotide deletion spanning nucleotides 501–550 results in a total free energy of −127.2 kcal/mol (SEQ ID NO:3), whereas a 50 nucleotide deletion at nucleotides 551–600 (SEQ ID NO:4) results in an RNA structure with −118.9 kcal/mol of free energy indicating the importance of the size of the deletion and location in ultimately defining mRNA secondary structure. Larger deletions, in different portions of the 401–624 region of the 5' UTR, yield RNA structures with varying predicted energy states (SEQ ID NOS:5–7). These results are summarized in Table 3.

TABLE 3

SEQUENCE VARIATION IN 5' UTR-EFFECT ON mRNA FREE ENERGY

| Sequence | SEQ ID NO: | Nucleotide Length (bp) | Region of Deletion | Number of Nucleotide Deleted (bp) | Free Energy (kal/mol) |
|---|---|---|---|---|---|
| Native | 2 | 224 | — | — | −161.0 |
| 5'a | 3 | 174 | 501–550 | 50 | −127.2 |
| 5'b | 4 | 174 | 551–600 | 50 | −118.9 |
| 5'c | 5 | 124 | 401–550 | 100 | −94.1 |
| 5'd | 6 | 74 | 401–550 | 150 | −52.3 |
| 5'e | 7 | 34 | 401–590 | 190 | −11.3 |

Likewise, for example, the free energy for the RNA secondary structure for nucleotides 2773–2972 in the 3' UTR of the EPO gene is predicted to be −81.4 kcal/mol (SEQ ID NO:8). A 50 nucleotide deletion spanning nucleotides 2923–2972 (SEQ ID NO:9) results in a total free energy of −53.5 kcal/mol, whereas a 100 nucleotide deletion at nucleotides 2873–2972 (SEQ ID NO:10) results in an RNA structure with −33.3 kcal/mol of free energy. Larger deletions, in different portions of the 2773–2973 region of the 3' UTR, yield RNA structures with varying predicted energy states (SEQ ID NOS:11 and 12). These results are summarized in Table 4.

TABLE 4

SEQUENCE VARIATION IN 3' UTR-EFFECT ON mRNA FREE ENERGY

| Sequence | SEQ ID NO: | Nucleotide Length (bp) | Region of Deletion | Number of Nucleotide Deleted (bp) | Free Energy (kal/mol) |
|---|---|---|---|---|---|
| Native | 8 | 200 | — | — | −81.4 |
| 3'a | 9 | 150 | 2923–2972 | 50 | −53.5 |
| 3'b | 10 | 100 | 2873–2972 | 100 | −33.3 |
| 3'c | 11 | 50 | 2823–2972 | 150 | −12.5 |
| 3'd | 12 | 100 | 2801–2900 | 100 | −36.6 |

The secondary structure of mRNA affects the rates of translation of the corresponding coding regions (Kikinis, Z., et al., *Nucleic Acids Res.* 23: 4190–4195, 1995; Kozak, M., *Mamm. Genome* 7: 563–574, 1996; Bettany, A. J., et al., *J. Biol. Chem.* 267: 16531–16537, 1992; Kozak, M., *J. Mol. Biol.* 235: 95–110, 1994). Secondary structure loops in the mRNA must be unwound to facilitate ribosome attachment and proper protein assembly (Alberts, B., et al., "*Molecular Biology of the Cell*", 3rd ed., Garland Publishing, Inc., New York, N.Y., pp. 223–290, 1994).

The nascent polypeptide chains can interact with chaperon proteins, for example, BiP, in unique ways which can affect the proper folding of the polypeptide chain and influence passage of the protein through the endoplasmic reticulum thereby altering glycosylation of the resulting protein. Recent data suggest that BiP-like proteins not only bind improperly folded proteins but also may assist in the appropriate protein folding and facilitate the membrane translocation and glycosylation of secretory proteins (Knittler, M. R., et al., *EMBO J.*11:1573–1581, (1992); Sanders, S. L. et al., *Cell* 69:353–365, (1992)).

Alterations in glycosylation patterns can influence the secretion and, in the case of EPO, drastically alter biological activity (Yamaguchi, K., et al., *J. Biol. Chem.* 266:20434–20439, 1991).

The three dimensional structure of a polypeptide, for example EPO, is significantly influenced by the protein backbone and the oligosaccharide chains. Alterations in the carbohydrate composition (e.g., the number of N- or O-linked oligosaccharide residues and/or type of sugar moieties) can lead to different biological properties of the polypeptide variant proteins and, thus, varied therapeutic effects. Therefore, a difference in the 5' or 3' UTR can affect mRNA secondary structure, which in turn can influence the rate of expression and post-translational modifications such as glycosylation. The proper glycosylation of a polypeptide can be of paramount importance to proper folding and secretion of the mature product and, hence, its biological and pharmacological properties.

Indices of intrinsic structural variations in the recombinant polypeptide variant proteins can be manifested in differences in the three-dimensional structure of the protein backbone and the extent and pattern of carbohydrate chains. For example, circular dichroism (CD) spectra and thermal stability for the resulting polypeptide variants can be performed to determine the content of alpha helix, beta sheet, beta turn and random coil for different glycoproteins. The structure of the oligosaccharide chains can be determined, for example, using enzymatic and chemical deglycosylation, gas chromatography, methylation analyses, fast-atom-bombardment mass spectrometry as well as one-and two-dimensional $^1$H-NMR spectrometry. The methods to per-form the above mentioned analyses are routine to one of ordinary skill in the art and are delineated in detail in several references including for example, Ausubel, F. M., et al., "Current Protocols in Molecular Biology" (1995); Nimtz, M., et al. *Eur. J. Biochem.* 213: 39–56, 1993; and Nimtz, M., et al., *FEBS* 365: 203–208, 1995, the teachings of which are herein incorporated by reference in their entirety.

In addition, assessment of the structural differences in the recombinant polypeptide variant proteins could be evaluated using immunoprecipitation with polypeptide-specific monoclonal antibodies and heat denaturation curves. Experimental techniques to measure these properties of a polypeptide, for example, EPO, are described in Sytkowski and Grodberg (U.S. Pat. No. 5,614,184); Sytkowski (U.S. Pat. No. 5,580,853); and Powell (U.S. Pat. No. 5,688,679); the teachings of which are herein incorporated by reference in their entirety.

EXAMPLE 5

OLIGONUCLEOTIDE-DIRECTED MUTAGENESIS OF RECOMBINANT POLYPEPTIDES

Recombinant polypeptide, for example EPO, variant proteins can be prepared using oligonucleotide-directed mutagenesis according to the Altered Sites™ In Vitro Mutagenesis System kit (Promega Corporation of Madison, Wis.). The Altered Sites™ System is based on experimental protocols routine to one of ordinary skill in the art of molecular biology. The kit consists of a unique mutagenesis vector and a simple, straightforward procedure for selection of oligonucleotide-directed mutants. The system is based on the use of a second mutagenic oligonucleotide to confer antibiotic resistance to the mutant DNA strand. The system employs a phagemid vector, pSELECT-1, which contains two genes for antibiotic resistance. One of these genes, for tetracycline resistance, is always functional. The other, for ampicillin resistance, is inactivated. An oligonucleotide is provided which restores ampicillin resistance to the mutant strand during the mutagenesis reaction. This oligonucleotide is annealed to the single-stranded DNA (ssDNA) template at the same time as the mutagenic oligonucleotide and subsequent synthesis and ligation of the mutant strand links the two. The DNA is transformed into a repair minus strain *E. coli*, or other suitable host, and the cells are grown in the presence of ampicillin, yielding large numbers of colonies. A second round of transformation in JM109, or a similar host, ensures proper segregation of mutant and wild type plasmids and results in a high proportion of mutants.

The pSELECT-1 plasmid is a phagemid, defined as a chimeric plasmid containing the origin of a single-stranded DNA bacteriophage. This phagemid produces ssDNA upon infection of the host cells with the helper phage R408 or M13KO7. The vector contains a multiple cloning site flanked by the SP6 and T7 RNA polymerase promoters and is inserted into the lacZ α-peptide. Cloning of a DNA insert into the multiple cloning site results in inactivation of the α-peptide. When plated on indicator plates, colonies containing recombinant plasmids are white in a background of blue colonies. The SP6 and T7 promoters may be used to generate high specific activity RNA probes from either strand of the insert DNA. These sites also serve as convenient priming sites for sequencing of the insert. The pSELECT-1 vector carries gene sequences for both ampicillin and tetracycline resistance. However, the plasmid is ampicillin sensitive because a frameshift is introduced into this resistance gene by removing the Pst I site. Therefore, propagation of the plasmid and recombinants is performed under tetracycline selection.

The pSELECT-Control vector provides a convenient white/blue positive control for mutagenesis reactions. This vector is derived from the pSELECT-1 vector by removing the Pst I site within the polylinker. The resultant frameshift in the lac α-peptide inactivated β-galactosidase and leds to a white colony phenotype on indicator plates. A lacZ repair oligonucleotide (supplied with the system) may be used to introduce a four base insertion which corrects the defect in the lacZ gene and restores colony color to blue. The fraction of blue colonies obtained is an indication of the mutagenesis efficiency. When the lacZ repair oligonucleotide is used in combination with the ampicillin repair oligonucleotide to correct this defect, 80–90% of the ampicillin resistant colonies are blue. When the lacZ repair oligonucleotide is used alone, a mutagenesis efficiency of only 2–5% is seen.

The mutagenic oligonucleotide must be complementary to the single-stranded target DNA. The ssDNA produced by the pSELECT-1 phagemid is complementary to the lacZ coding strand.

The stability of the complex between the oligonucleotide and the template is determined by the base composition of the oligonucleotide and the conditions under which it is annealed. In general, a 17–20 base oligonucleotide with the mismatch located in the center is sufficient for single base mutations. This provides 8–10 perfectly matched nucleotides on either side of the mismatch. For mutations involving two or more mismatches, oligonucleotides of 25 bases or longer are needed to allow for 12–15 perfectly matched nucleotides on either side of the mismatch.

Routinely, oligonucleotides are annealed by heating to 70° C. for 5 minutes followed by slow cooling to room temperature.

DNA to be mutated is cloned into the pSELECT-1 vector using the multiple cloning sites. The vector DNA is then transformed into competent cells of JM109, or a similar host, and recombinant colonies are selected by plating on LB plates containing 15 μg/ml tetracycline, 0.5 mM IPTG, and 40 μg/ml X-Gal. After incubation for 24 hours at 37° C., colonies containing recombinant plasmids appear white in a background of blue colonies.

To produce single-stranded template for the mutagenesis reaction, individual colonies containing pSELECT-Control or recombinant pSELECT-1 phagemids are grown and the cultures are infected with helper phage as described below. The single-stranded DNA produced is complementary to the lacZ coding strand and complementary to the strand of the multiple cloning site. Two helper phages R408 and M13KO7 are used to provide the greatest latitude in optimizing ssDNA yields.

EXAMPLE 6

EVALUATION OF BIOLOGICAL ACTIVITY OF RECOMBINANT POLYPEPTIDE VARIANT PROTEINS

The biological activity of the recombinant polypeptide variants is determined using in vitro and in vivo assays.

The recombinant polypeptide variant proteins are preferably purified substantially prior to use, particularly where the protein could be employed as an in vivo therapeutic, although the degree of purity is not necessarily critical where the molecule is to be used in vitro. In one embodiment, the recombinant polypeptides can be isolated to about 50% purity (by weight), more preferably to about 80% by weight or about 95% by weight. It is most preferred to utilize a protein which is essentially pure (e.g., about 99% by weight or to homogeneity) for in vitro and in vivo assays as well as in vivo therapeutics.

For example, recombinant EPO variant proteins, which are prepared according to the methods discussed in Example 4, can be screened for in vitro and in vivo activity prior to use in therapeutic settings. The in vitro assay measures the effect of EPO variant proteins on erythropoiesis in intact mouse spleen cells assay according to the procedure of Krystal, G., *Exp. Hematol.*, 11:649–660 (1983). To screen the various recombinant EPO variant proteins for activity, for example, in vitro or in vivo, the proteins (or mixtures of the EPO proteins) can be evaluated for the extent of hematopoieses, platelet production or receptor binding. Tests to determine biological activity are well-known to those of skill in the art. For example, the biological activity of EPO can be measured as described in Sytkowski and Grodberg (U.S. Pat. No. 5,614,184); Sytkowski (U.S. Pat. No. 5,580,853); Sytkowski, U.S. patent application "Modified Polypeptides with Increased Biological Activity", filed Feb. 3, 1998; and Powell (U.S. Pat. No. 5,688,679); the teachings of which are herein incorporated by reference in their entirety.

EQUIVALENTS

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

What is claimed is:

1. A nucleic acid molecule encoding a fusion protein, wherein the fusion protein comprises the amino acid sequence of two or more erythropoietin polypeptides, and wherein the nucleic acid molecule comprise a 5' noncoding sequence comprising SEQ ID NOS: 3 or 4.

2. The nucleic acid molecule of claim 1, wherein the fusion protein further comprises a peptide linker sequence between at least one pair of the erythropoietin polypeptide sequences.

3. The isolated nucleic acid molecule of claim 2, wherein said peptide linker allows the erythropoietin proteins to rotate relative to each other.

4. The isolated nucleic acid molecule of claim 3, wherein said peptide linker is from about 10 amino acids to about 20 amino acids in length.

5. The isolated nucleic acid molecule of claim 3, wherein the peptide linker is about 15 amino acids in length.

6. The isolated nucleic acid molecule of claim 3, wherein the peptide linker comprises amino acids selected from the group consisting of glycine, serine, asparagine, threonine and alanine.

7. A nucleic acid molecule encoding a fusion protein, wherein the fusion protein comprises the amino acid sequence of two or more erythropoietin polypeptides, and wherein the nucleic acid molecule comprises a 3' noncoding sequence comprising SEQ ID NO: 12.

8. The nucleic acid molecule of claim 7, wherein the fusion protein further comprises a peptide linker sequence between at least one pair of the etythropoietin polypeptide sequences.

9. The isolated nucleic acid molecule of claim 8, wherein said peptide linker allows the erythropoietin proteins to rotate relative to each other.

10. The isolated nucleic acid molecule of claim 9, wherein said peptide linker is from about 10 amino acids to about 20 amino acids in length.

11. The isolated nucleic acid molecule of claim 9, wherein the peptide linker is about 15 amino acids in length.

12. The isolated nucleic acid molecule of claim 9, wherein the peptide linker comprises amino acids selected from the group consisting of glycine, serine, asparagine, threonine and alanine.

13. The nucleic acid molecule of claim 1, wherein the nucleic acid molecule further comprises a 3' noncoding sequence comprising SEQ ID NO: 12.

14. The nucleic acid molecule of claim 13, wherein the fusion protein further comprises a peptide linker sequence between at least one pair of the erythropoietin polypeptide sequences.

15. The isolated nucleic acid molecule of claim 14, wherein said peptide linker allows the erythropoietin proteins to rotate relative to each other.

16. The isolated nucleic acid molecule of claim 15, wherein said peptide linker is from about 10 amino acids to about 20 amino acids in length.

17. The isolated nucleic acid molecule of claim 15, wherein the peptide linker is about 15 amino acids in length.

18. The isolated nucleic acid molecule of claim 15, wherein the peptide linker comprises amino acids selected from the group consisting of glycine, serine, asparagine, threonine and alanine.

19. A recombinant host cell comprising a nucleic acid molecule encoding a fusion protein, wherein the fusion protein comprises the amino acid sequence of two or more erythropoietin polypeptides, and wherein the nucleic acid molecule comprises a 5' noncoding sequence comprising SEQ ID NOS: 3 or 4.

20. A recombinant host cell comprising the nucleic acid molecule of claim 19, wherein at least one of the nucleic acid molecules further comprises a 3' noncoding sequence comprising SEQ ID NO: 12.

21. A recombinant host cell comprising a nucleic acid molecule encoding a fusion protein, wherein the fusion protein comprises the amino acid sequence of two or more erythropoietin polypeptides, and wherein the nucleic acid molecule comprises a 3' noncoding sequence comprising SEQ ID NO: 12.

22. A vector comprising the nucleic acid molecule of claim 1.

23. A vector comprising the isolated nucleic acid molecule of claim 7.

24. A vector comprising the isolated nucleic acid molecule of claim 13.

25. A method for making an erythropoietin fusion protein, comprising the steps of:
   a) transfecting a recombinant host cell with a vector comprising a nucleic acid molecule encoding a fusion protein, wherein the fusion protein comprises the amino acid sequence of two or more erythropoietin polypeptides, and wherein the nucleic acid molecule comprises a 5' noncoding sequence comprising SEQ ID NOS: 3 or 4; and
   b) culturing the recombinant host cell in a suitable medium to produce the erythropoietin fusion protein.

26. The method of claim 25, further comprising recovering the erythropoietin fusion protein from the suitable medium.

27. The method of claim 26, further comprising combining the recovered erythropoietin fusion protein with a pharmaceutically acceptable carrier to produce a pharmaceutical composition.

28. A method of treating a subject comprising producing a pharmaceutical composition according to the method of claim 27 and administering the composition to the subject.

29. A method for making an erythropoietin fusion protein, comprising the steps of:
   a) transfecting a recombinant host cell with a vector comprising a nucleic acid molecule encoding a fusion protein, wherein the fusion protein comprises the amino acid sequence of two or more erythropoietin polypeptides, and wherein the nucleic acid molecule comprises a 3' noncoding sequence comprising SEQ ID NO: 12; and
   b) culturing the recombinant host cell in a suitable medium to produce the erythropoietin fusion protein.

30. The method of claim 29, further comprising recovering the erythropoietin fusion protein from the suitable medium.

31. The method of claim 30, further comprising combining the recovered erythropoietin fusion protein with a pharmaceutically acceptable carrier to produce a pharmaceutical composition.

32. A method of treating a subject comprising producing a pharmaceutical composition according to the method of claim 31 and administering the composition to the subject.

33. A method for making an erythropoietin fusion protein, comprising the steps of:
   a) transfecting a recombinant host cell with a vector comprising a nucleic acid molecule encoding a fusion protein, wherein the fusion protein comprises the amino acid sequence of two or more erythropoietin polypeptides, and wherein the nucleic acid molecule comprises a 5' noncoding sequence comprising SEQ ID NOS: 3 or 4 and further comprises a 3' noncoding sequence comprising SEQ ID NO: 12; and
   b) culturing the recombinant host cell in a suitable medium to produce the erythropoietin fusion protein.

34. The method of claim 33, further comprising recovering file erythropoietin fusion protein from the suitable medium.

35. The method of claim 34, further comprising combining the recovered erythropoietin fusion protein with a pharmaceutically acceptable carrier to produce a pharmaceutical composition.

36. A method of treating a subject comprising producing a pharmaceutical composition according to the method of claim 35 and administering the composition to the subject.

* * * * *

UNITED STATES PATENT AND TRADEMARK OFFICE
CERTIFICATE OF CORRECTION

PATENT NO. : 6,187,564
DATED : February 13, 2001
INVENTOR(S) : Arthur J. Sytkowski It is certified that error appears in the above-identified patent and that said Letters Patent is hereby corrected as shown below:

Claim 34, Column 38, at Line 27, delete the word "file" and substitute the word - - the- - therefor.

Signed and Sealed this

Twenty-ninth Day of May, 2001

Attest:

NICHOLAS P. GODICI

*Attesting Officer*    *Acting Director of the United States Patent and Trademark Office*

SEQUENCE LISTING

```
<160> NUMBER OF SEQ ID NOS: 24

<210> SEQ ID NO 1
<211> LENGTH: 3602
<212> TYPE: DNA
<213> ORGANISM: Human

<400> SEQUENCE: 1
aagcttctgg gcttccagac ccagctactt tgcggaactc agcaacccag gcatctctga      60
gtctccgccc aagaccggga tgcccccag gggaggtgtc cgggagccca gcctttccca     120
gatagcacgc tccgccagtc ccaagggtgc gcaaccggct gcactcccct cccgcgaccc     180
agggcccggg agcagccccc atgacccaca cgcacgtctg cagcagcccc gctcacgccc     240
cggcgagcct caacccaggc gtcctgcccc tgctctgacc ccgggtggcc cctaccctg      300 gcgacccctc acgcacacag cctctccccc accccaccc gcgcacgcac acatgcagat     360
aacagccccg accccggcc agagccgcag agtccctggg ccaccccggc cgctcgctgc     420
gctgcgccgc accgcgctgt cctcccggag ccggaccggg gccaccgcgc ccgctctgct     480
ccgacaccgc gccccctgga cagccgccct ctcctctagg cccgtggggc tggccctgca     540
ccgccgagct tcccgggatg agggcccccg gtgtggtcac ccggcgcgcc ccaggtcgct     600
gagggacccc ggccaggcgc ggagatgggg gtgcacggtg agtactcgcg ggctgggcgc     660
tcccgccgcc cgggtccctg tttgagcggg gatttagcgc cccggctatt ggccaggagg     720
tggctgggtt caaggaccgg cgacttgtca aggacccccgg aaggggggagg ggggtgggggc   780 agcctccacg tgccagcggg gacttggggg agtccttggg gatggcaaaa acctgacctg     840
tgaaggggac acagtttggg ggttgagggg aagaaggttt gggggttctg ctgtgccagt     900
ggagaggaag ctgataagct gataacctgg gcgctggagc caccacttat ctgccagagg     960
ggaagcctct gtcacaccag gattgaagtt tggccggaga agtggatgct ggtagctggg    1020
ggtggggtgt gcacacggca gcaggattga atgaaggcca gggaggcagc acctgagtgc    1080
ttgcatggtt ggggacagga aggacgagct ggggcagaga cgtggggatg aaggaagctg    1140
tccttccaca gccaccttc tccctccccg cctgactctc agcctggcta tctgttctag     1200
aatgtcctgc ctggctgtgg cttctcctgt ccctgctgtc gctccctctg ggcctcccag    1260
tcctgggcgc cccaccacgc ctcatctgtg acagccgagt cctggagagg tacctcttgg    1320
```

-continued

```
aggccaagga ggccgagaat atcacggtga gaccccttcc ccagcacatt ccacagaact    1380
cacgctcagg gcttcaggga actcctccca gatccaggaa cctggcactt ggtttgggt     1440
ggagttggga agctagacac tgcccccta cataagaata agtctggtgg ccccaaacca     1500
tacctggaaa ctaggcaagg agcaaagcca gcagatccta cggcctgtgg gccagggcca    1560
gagccttcag ggaccttga ctccccgggc tgtgtgcatt tcagacgggc tgtgctgaac     1620
actgcagctt gaatgagaat atcactgtcc cagacaccaa agttaatttc tatgcctgga    1680
agaggatgga ggtgagttcc ttttttttt tttttccttt cttttggaga atctcatttg     1740
cgagcctgat tttggatgaa agggagaatg atcgggggaa aggtaaaatg gagcagcaga    1800
gatgaggctg cctgggcgca gaggctcacg tctataatcc caggctgaga tggccgagat    1860
gggagaattg cttgagccct ggagtttcag accaacctag gcagcatagt gagatccccc    1920
atctctacaa acatttaaaa aaattagtca ggtgaagtgg tgcatggtgg tagtcccaga    1980
tatttggaag gctgaggcgg gaggatcgct tgagcccagg aatttgaggc tgcagtgagc    2040
tgtgatcaca ccactgcact ccagcctcag tgacagagtg aggccctgtc tcaaaaaaga    2100
aaagaaaaaa gaaaaataat gagggctgta tggaatacat tcattattca ttcactcact    2160
cactcactca ttcattcatt cattcattca acaagtctta ttgcatacct tctgtttgct    2220
cagcttggtg cttggggctg ctgaggggca ggagggagag ggtgacatgg gtcagctgac    2280
tcccagagtc cactccctgt aggtcgggca gcaggccgta gaagtctggc agggcctggc    2340
cctgctgtcg gaagctgtcc tgcggggcca ggccctgttg gtcaactctt cccagccgtg    2400
ggagcccctg cagctgcatg tggataaagc cgtcagtggc cttcgcagcc tcaccactct    2460
gcttcgggct ctgggagccc aggtgagtag gagcggacac ttctgcttgc cctttctgta    2520
agaaggggag aagggtcttg ctaaggagta caggaactgt ccgtattcct tccctttctg    2580
tggcactgca gcgacctcct gttttctcct tggcagaagg aagccatctc ccctccagat    2640
gcggcctcag ctgctccact ccgaacaatc actgctgaca ctttccgcaa actcttccga    2700
gtctactcca atttcctccg gggaaagctg aagctgtaca caggggaggc ctgcaggaca    2760
ggggacagat gaccaggtgt gtccacctgg gcatatccac cacctccctc accaacattg    2820
cttgtgccac accctccccc gccactcctg aaccccgtcg aggggctctc agctcagcgc    2880
cagcctgtcc catggacact ccagtgccag caatgacatc tcaggggcca gaggaactgt    2940
ccagagagca actctgagat ctaaggatgt cacagggcca acttgagggc ccagagcagg    3000
aagcattcag agagcagctt taaactcagg gacagagcca tgctgggaag acgcctgagc    3060
tcactcggca ccctgcaaaa tttgatgcca ggacacgctt tggaggcgat ttacctgttt    3120
tcgcacctac catcagggac aggatgacct ggagaactta ggtggcaagc tgtgacttct    3180
ccaggtctca cgggcatggg cactcccttg gtggcaagag ccccttgac accggggtgg    3240
tgggaaccat gaagacagga tggggctgg cctctggctc tcatgggtc caagttttgt     3300
gtattcttca acctcattga caagaactga accaccaat atgactcttg cttttctgt     3360
tttctgggaa cctccaaatc ccctggctct gtcccactcc tggcagcagt gcagcaggtc    3420
caggtccggg aaatgagggg tggagggggc tgggccctac gtgctgtctc acacagcctg    3480
tctgacctct cgacctaccg gcctaggcca caagctctgc ctacgctggt caataaggtg    3540
tctccattca aggcctcacc gcagtaaggc agctgccaac cctgcccagg gcaaggctgc    3600
ag                                                                  3602
```

```
<210> SEQ ID NO 2
<211> LENGTH: 224
<212> TYPE: DNA
<213> ORGANISM: Human

<400> SEQUENCE: 2 ccacccggc cgctcgctgc gctgcgccgc accgcgctgt cctcccggag ccggaccggg     60
gccaccgcgc ccgctctgct ccgacaccgc gcccctgga cagccgccct ctcctctagg    120
cccgtggggc tggccctgca ccgccgagct tcccgggatg agggccccg gtgtggtcac    180 ccggcgcgcc ccaggtcgct gagggacccc ggccaggcgc ggag                    224

<210> SEQ ID NO 3
<211> LENGTH: 174
<212> TYPE: DNA
<213> ORGANISM: Human

<400> SEQUENCE: 3 ccacccggc cgctcgctgc gctgcgccgc accgcgctgt cctcccggag ccggaccggg     60
gccaccgcgc ccgctctgct ccgacaccgc gcccctgga tcccgggatg agggccccg    120 gtgtggtcac ccggcgcgcc ccaggtcgct gagggacccc ggccaggcgc ggag         174

<210> SEQ ID NO 4
<211> LENGTH: 174
<212> TYPE: DNA
<213> ORGANISM: Human

<400> SEQUENCE: 4 ccacccggc cgctcgctgc gctgcgccgc accgcgctgt cctcccggag ccggaccggg     60
gccaccgcgc ccgctctgct ccgacaccgc gcccctgga cagccgccct ctcctctagg    120
cccgtggggc tggccctgca ccgccgagct gagggacccc ggccaggcgc ggag         174

<210> SEQ ID NO 5
<211> LENGTH: 124
<212> TYPE: DNA
<213> ORGANISM: Human

<400> SEQUENCE: 5
cagccgccct ctcctctagg cccgtggggc tggccctgca ccgccgagct tcccgggatg     60 agggccccg gtgtggtcac ccggcgcgcc ccaggtcgct gagggacccc ggccaggcgc    120
ggag                                                                 124

<210> SEQ ID NO 6
<211> LENGTH: 74
<212> TYPE: DNA
<213> ORGANISM: Human

<400> SEQUENCE: 6
tcccgggatg agggccccg gtgtggtcac ccggcgcgcc ccaggtcgct gagggacccc     60
ggccaggcgc ggag                                                      74

<210> SEQ ID NO 7
<211> LENGTH: 34
<212> TYPE: DNA
<213> ORGANISM: Human

<400> SEQUENCE: 7
ccaggtcgct gagggacccc ggccaggcgc ggag                                34
```

```
<210> SEQ ID NO 8
<211> LENGTH: 200
<212> TYPE: DNA
<213> ORGANISM: Human

<400> SEQUENCE: 8
ccaggtgtgt ccacctgggc atatccacca cctccctcac caacattgct tgtgccacac      60
cctcccccgc cactcctgaa ccccgtcgag gggctctcag ctcagcgcca gcctgtccca     120
tggacactcc agtgccagca atgacatctc aggggccaga ggaactgtcc agagagcaac     180
tctgagatct aaggatgtca                                                 200

<210> SEQ ID NO 9
<211> LENGTH: 150
<212> TYPE: DNA
<213> ORGANISM: Human

<400> SEQUENCE: 9
ccaggtgtgt ccacctgggc atatccacca cctccctcac caacattgct tgtgccacac      60
cctcccccgc cactcctgaa ccccgtcgag gggctctcag ctcagcgcca gcctgtccca     120
tggacactcc agtgccagca atgacatctc                                      150

<210> SEQ ID NO 10
<211> LENGTH: 100
<212> TYPE: DNA
<213> ORGANISM: Human

<400> SEQUENCE: 10
ccaggtgtgt ccacctgggc atatccacca cctccctcac caacattgct tgtgccacac      60
cctcccccgc cactcctgaa ccccgtcgag gggctctcag                           100

<210> SEQ ID NO 11
<211> LENGTH: 50
<212> TYPE: DNA
<213> ORGANISM: Human

<400> SEQUENCE: 11
ccaggtgtgt ccacctgggc atatccacca cctccctcac caacattgct                 50

<210> SEQ ID NO 12
<211> LENGTH: 100
<212> TYPE: DNA
<213> ORGANISM: Human

<400> SEQUENCE: 12
ccaggtgtgt ccacctgggc atatccaccc agtgccagca atgacatctc aggggccaga      60
ggaactgtcc agagagcaac tctgagatct aaggatgtca                           100

<210> SEQ ID NO 13
<211> LENGTH: 17
<212> TYPE: DNA
<213> ORGANISM: Human
<220> FEATURE:
<223> OTHER INFORMATION: DNA primer

<400> SEQUENCE: 13
aggggsgggg sggggst                                                     17

<210> SEQ ID NO 14
```

```
<211> LENGTH: 20
<212> TYPE: DNA
<213> ORGANISM: Human

<400> SEQUENCE: 14
gccggcggtg gtggatctgg                                          20

<210> SEQ ID NO 15
<211> LENGTH: 22
<212> TYPE: DNA
<213> ORGANISM: Human

<400> SEQUENCE: 15
aggcgcggag atgggggtgc ac                                       22

<210> SEQ ID NO 16
<211> LENGTH: 40
<212> TYPE: DNA
<213> ORGANISM: Human

<400> SEQUENCE: 16
ccagatccac caccgccggc tctgtccccct gtcctgcagg                   40
```

Note: the original is "ccagatccac caccgccggc tctgtccct gtcctgcagg" — reading carefully:

```
ccagatccac caccgccggc tctgtccct gtcctgcagg                    40

<210> SEQ ID NO 17
<211> LENGTH: 40
<212> TYPE: DNA
<213> ORGANISM: Human

<400> SEQUENCE: 17
cgccaccgga tccaccgcca ccagatccac caccgccggc                    40

<210> SEQ ID NO 18
<211> LENGTH: 40
<212> TYPE: DNA
<213> ORGANISM: Human

<400> SEQUENCE: 18
tggtggggca gtactgccgc cgccaccgga tccacccgcc                    40

<210> SEQ ID NO 19
<211> LENGTH: 38
<212> TYPE: DNA
<213> ORGANISM: Human

<400> SEQUENCE: 19
gcggcagtac tgccccacca cgcctcatct gtgacagc                      38

<210> SEQ ID NO 20
<211> LENGTH: 22
<212> TYPE: DNA
<213> ORGANISM: Human

<400> SEQUENCE: 20
caggtggaca cacctggtca tc                                       22

<210> SEQ ID NO 21
<211> LENGTH: 20
<212> TYPE: DNA
<213> ORGANISM: Human

<400> SEQUENCE: 21
gccggcggtg gtggatctgg                                          20
```

```
<210> SEQ ID NO 22
<211> LENGTH: 40
<212> TYPE: DNA
<213> ORGANISM: Human

<400> SEQUENCE: 22
gccggcggtg gtggatctgg tggcggtgga tccggtggcg                              40

<210> SEQ ID NO 23
<211> LENGTH: 60
<212> TYPE: DNA
<213> ORGANISM: Human

<400> SEQUENCE: 23
gccggcggtg gtggatctgg tggcggtgga tccggtggcg gcggcagtac tgccccacca       60

<210> SEQ ID NO 24
<211> LENGTH: 11
<212> TYPE: DNA
<213> ORGANISM: Artificial Sequence
<220> FEATURE:
<223> OTHER INFORMATION: DNA prmier

<400> SEQUENCE: 24
gcggcagtac t                                                            11
```